(12) United States Patent
Pavlakis et al.

(10) Patent No.: US 6,919,442 B1
(45) Date of Patent: Jul. 19, 2005

(54) NUCLEIC ACIDS COMPRISING A POST-TRANSCRIPTIONAL REGULATORY ELEMENT (PRE) AND THEIR USES

(75) Inventors: George N. Pavlakis, Rockville, MD (US); Filomena Nappi, Rome (IT)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/673,716

(22) PCT Filed: May 18, 1999

(86) PCT No.: PCT/US99/11082

§ 371 (c)(1),
(2), (4) Date: Feb. 26, 2001

(87) PCT Pub. No.: WO99/61596

PCT Pub. Date: Dec. 2, 1999

Related U.S. Application Data

(60) Provisional application No. 60/086,487, filed on May 22, 1998.

(51) Int. Cl.[7] .............................................. C07H 21/04
(52) U.S. Cl. ................................ 536/23.72; 424/185.1; 424/188.1; 424/199.1; 424/207.1; 424/208.1; 536/23.1; 536/24.1
(58) Field of Search ........................... 536/23.72, 24.1, 536/23.1; 424/207.1, 208.1, 185.1, 188.1, 199.1

(56) References Cited

PUBLICATIONS

Fox et al. No winners against AIDS, Bio/Technology (1994) vol. 12, pp. 128.*
Gene Bank Accession # C80740 and C80177.*

Nkengasong et al. Dual infection with human immunodeficiency virus type 1 and type 2 : impact on HIV type 1 viral load and immune activation markers in HIV–seropositve female sex workers in Abidjan, Ivory Coast. AIDS Research and Human Retroviruses (2000).*

Greenberg AE. Possible protective effect of HIV–2 against incident HIV–1 infection: review of available epidemiological and in vitro data. AIDS (2001) vol. 15, No. 17, pp. 2319–2321.*

Macola et al. Aids vaccine : are we ready for human efficacy trials ? Journal of the American Medical association (1994) vol. 272, No. 6, pp. 488–489.*

Feinberg et al. Aids Vaccine Models : challenging challenge viruses. Nature Medicine (2002) vol. 8, pp. 207–210.*

* cited by examiner

*Primary Examiner*—Ulrike Winkler
(74) *Attorney, Agent, or Firm*—Townsend and Townsend and Crew LLP

(57) ABSTRACT

The invention provides a novel post-transcriptional regulatory element that can function as an RNA nucleo-cytoplasmic transport element. The invention also provides for an attenuated HIV-1 hybrid virus for use as a vaccine and a kit incorporating the hybrid virus. The kit also includes instructional material teaching the use of the vaccine, where the instructional material indicates that the vaccine is used for the prophylaxis or amelioration of HIV-1 infection in a mammal; that the vaccine is to be administered to a mammal in a therapeutically effective amount sufficient to express a viral protein; where the vaccine will not cause clinically significant $CD4^+$ cell depletion; and, the expression of the viral protein elicits an immune response to the attenuated HIV-1 virus. The invention further provides for a method for screening for post-transcriptional RNA nucleo-cytoplasmic transport element (NCTE) binding proteins.

30 Claims, No Drawings

NUCLEIC ACIDS COMPRISING A POST-TRANSCRIPTIONAL REGULATORY ELEMENT (PRE) AND THEIR USES

This application is the U.S. national phase of PCT/US99/11082 under 35 U.S.C. §371, which claims priority to U.S. Provisional Patent Application 60/086,487, filed May 22, 1998.

FIELD OF THE INVENTION

This invention pertains to the field of virology and vaccine development. In particular, this invention pertains to the discovery of a novel post-transcriptional regulatory element (PRE) that can function as a post-transcriptional RNA nucleo-cytoplasmic transport element (NCTE). This novel nucleic acid sequence can be used to construct an attenuated retrovirus.

BACKGROUND OF THE INVENTION

Infection with human immunodeficiency virus type 1 (HIV-1) is typically characterized by a progressive disintegration of the immune system, acquired immune deficiency syndrome (AIDS), and death. However, some individuals infected HIV-1 virus do not develop disabled immune systems or AIDS. Because a cure or vaccine for AIDS has eluded researchers for years, these individuals and the virus they harbor may provide essential clues toward the development of vaccines or treatments against HIV.

Some of these asymptomatic HIV-1 infected individuals have variant strains that affected the virus' ability to grow. Viral gene mutations were causing the HIV-1 to grow at a relatively slow rate (growth attenuation). The resultant low levels of virus created a non-lethal, asymptomatic infection (Iversen (1995) *J. of Virology* 69:5743–5753; Hua (1996) *Virology* 222:423–429).

Differences between the deadly form of the virus and the non-lethal variants were found in portions of the viral genome able to regulate how fast the virus and grows and multiplies. This creates an exciting new way to design an effective vaccine against HIV-1. Slow-growing, non-lethal (attenuated) viral mutants can be designed as vaccines to protect against AIDS. Thus, there exists a great need for new ways to attenuate retroviruses, such as HIV-1. The present invention fulfills this and other needs.

SUMMARY OF THE INVENTION

The invention provides a novel post-transcriptional regulatory element (PRE) that can function as a post-transcriptional RNA nucleo-cytoplasmic transport element (NCTE). The sequence was initially derived from a mouse genomic nucleotide sequence. Sequence analysis found that the novel PRE has significant homology to intracisternal A-type particle (IAP) sequences.

The invention provides a novel family of isolated nucleic acids consisting of a post-transcriptional regulatory element (PRE) nucleic acid defined as having the following properties: the PRE nucleic acid, when inserted in a recombinant, hybrid HIV-1, is capable of functioning as a post-transcriptional RNA nucleo-cytoplasmic transport element (NCTE) in place of wild-type NCTE in the hybrid HIV-1, and when the PRE-containing hybrid HIV-1 virus infects activated human peripheral blood mononuclear cells (huPBMCs), the level of expression of HIV-1 p24$^{gag}$ is between about 5 fold and about 200 fold less than levels of p24$^{gag}$ expression when HIV-1 wild type virus, utilizing wild-type NCTE, infects activated huPBMCs; and, the PRE has at least 80% nucleic acid sequence identity to the sequence as set forth in SEQ ID NO:1. In other embodiments, the isolated PRE nucleic acid can have at least 90% nucleic acid sequence identity to the sequence as set forth in SEQ ID NO:1, and can comprise a sequence as set forth in SEQ ID NO:1. In another embodiment, when a PRE-containing hybrid HIV-1 virus infects activated huPBMCs, the level of expression of HIV-1 p$_{24}$$^{gag}$ is between about 10 fold and about 50 fold less than levels of p$_{24}$$^{gag}$ expression when HIV-1 wild type virus infects activated huPBMCs.

The invention also provides an isolated transcription product of a PRE nucleic acid of the invention. The isolated transcription product can have at least 90% nucleic acid sequence identity to the sequence as set forth in SEQ ID NO:1, and can comprise a sequence as set forth in SEQ ID NO:1.

The invention provides an expression cassette comprising a nucleic acid encoding a PRE nucleic acid of the invention, wherein the PRE nucleic acid is operably linked to a promoter. The expression cassette, as defined below, can be an expression vector. The PRE of the expression cassette can have at least 90% nucleic acid sequence identity to the sequence as set forth in SEQ ID NO:1, and can comprise a sequence as set forth in SEQ ID NO:1. In one embodiment, the invention provides a transfected cell comprising a polynucleotide encoding a PRE nucleic acid of the invention and a non-naturally occurring nucleic acid sequence.

The invention provides a recombinant retrovirus, wherein the retrovirus either lacks or has non-functional endogenous post-transcriptional RNA nucleo-cytoplasmic transport elements (NCTEs), further comprising a PRE of the invention operatively inserted into the retrovirus, the PRE capable of acting as an exogenous functional NCTE to reconstitute the lacking or non-functional endogenous NCTE and to reconstitute the infectivity of the retrovirus in a mammalian cell. The PRE inserted in the recombinant retrovirus can have at least 90% nucleic acid sequence identity to the sequence as set forth in SEQ ID NO:1, or can comprises a sequence as set forth in SEQ ID NO:1. The recombinant retrovirus, when infecting activated huPBMCs, has a level of expression between about 10 fold and about 50 fold less than when HIV-1 wild type virus infects activated huPBMCs.

The recombinant virus of the invention can be HIV-1 and the NCTE can be RRE. In various embodiments, the insertion of the PRE in the retrovirus is in the 3' untranslated region of the virus, or is in or flanking the Nef region of an HIV-1 virus. The HIV-1 can further lack a functional Nef.

The invention provides a vaccine for the prophylaxis or amelioration of a viral infection in a mammal comprising an attenuated retrovirus, wherein the attenuated retrovirus, when administered as a vaccine in sufficient amounts is capable of eliciting an immune response to the retrovirus in a mammal with a functional immune system, wherein the attenuated retrovirus lacks an endogenous functional post-transcriptional RNA nucleo-cytoplasmic transport element (NCTE) and/or the ability to express an endogenous functional NCTE binding protein, and the attenuated retrovirus further comprises a PRE nucleic acid of the invention. The attenuated retrovirus of the vaccine can be HIV-1. The PRE can be inserted in the 3' untranslated region of the virus or can be inserted in or flanking the Nef region of an HIV-1 virus. The attenuated HIV-1 can further lack a functional Nef. The NCTE can be RRE and the NCTE binding protein can be Rev.

The invention provides a kit for the prophylaxis or amelioration of a virus infection in a mammal, the kit comprising a vaccine and a pharmacologically acceptable carrier, wherein the vaccine comprises an attenuated retrovirus, wherein the attenuated retrovirus, when administered as a vaccine in sufficient amounts is capable of eliciting an immune response to the retrovirus in a mammal with a functional immune system, wherein the attenuated retrovirus lacks an endogenous functional post-transcriptional RNA nucleo-cytoplasmic transport element (NCTE) and/or the ability to express an endogenous functional NCTE binding protein, and the attenuated retrovirus further comprises a PRE nucleic acid of the invention. The kit can further comprise an instructional material teaching the use of the vaccine, wherein the instructional material indicates that the vaccine is used for the prophylaxis or amelioration of HIV-1 infection in a mammal; that the vaccine is to be administered to a mammal in a therapeutically effective amount sufficient to express a viral protein; wherein the vaccine will not cause clinically significant $CD4^+$ cell depletion; and, the expression of the viral protein elicits an immune response to the attenuated HIV-1 virus.

The invention provides use of a PRE of the invention in the manufacture of a medicament for the prophylaxis or amelioration of a viral infection. The viral infection can be a HIV-1 infection.

The invention provides a method for eliciting an immune response to a virus in a mammal, comprising administering to a mammal a therapeutically effective amount of an attenuated recombinant virus, wherein the virus comprises a PRE of the invention.

The invention provides a method for screening for a post-transcriptional RNA nucleocytoplasmic transport element (NCTE) binding protein comprising the following steps: providing a composition comprising a PRE of the invention; contacting the composition with a test compound; and, measuring the ability of the test compound to bind the NCTE.

A further understanding of the nature and advantages of the present invention may be realized by reference to the remaining portions of the specification and claims.

All publications, Genbank sequences, patents and patent applications cited herein are hereby expressly incorporated by reference for all purposes.

DETAILED DESCRIPTION OF THE INVENTION

The present invention provides a novel family of post-transcriptional regulatory elements, or PRE. Specifically, the PREs of the invention can function as RNA nucleo-cytoplasmic transport elements (NCTE). The exemplary PRE of the invention (SEQ ID NO:1) was initially derived from a mouse genomic nucleic acid. Sequence comparison analysis shows that PRE sequences are highly homologous to intracisternal A particle (IAP) sequences.

In retroviruses, including HIV type 1 (HIV-1), simian retrovirus type 1 (SRV-1), SRV-2, and Mason-Pfizer monkey virus (MPMV) (the later three are type D simian retroviruses), the rate of viral growth can be controlled by changing the rate of expression of their RNA message. This strategy is a "post-transcriptional" means to regulate gene expression and viral growth. Specifically, these retroviruses need a special sequence on their RNA to effect nuclear transport of unspliced mRNA encoding structural proteins. This sequence, called a "post-transcriptional regulatory element" (PRE), typically acts by internally base-pairing, allowing the RNA molecule to fold into a unique, secondary structure (a "cis-acting element"). The folding patterns are highly structured and are commonly stem-loop, or hairpin structures. A soluble protein binds specifically to this RNA structure to aid in the transport of the message from the nucleus to the cytoplasm (in addition to other functions, including aiding in the splicing of the transcript).

Some retroviruses, such as Simian type D retroviruses, including SRV-1, do not encode their own trans-acting, NCTE-binding proteins and instead utilize cellular NCTE binding proteins. Other retroviruses, such as HIV-1, utilize a retrovirally-encoded NCTE RNA binding protein, called "Rev." HIV-1 regulates the expression of its structural proteins encoded by the gag/pol- and env-encoding transcript using this NCTE system. HIV-1's NCTE binding protein "Rev" interacts with a specific NCTE sequence, designated the "Rev-responsive element," or "RRE," contained in its gag/pol and env encoding transcript. HIV-1's RRE does not bind cellular NCTE-binding proteins. Rev interacts directly with RRE as part of the RNA export machinery which transports RRE-containing transcripts to the cytoplasm from the nucleus. As a result, Rev and RRE are needed to produce infectious virus.

HIV-1 lacking a functional Rev/RRE control system, while uninfectious, can be reconstituted with exogenous control elements. For example, when simian retroviral CTE (e.g., CTE from SRV-1, SRV-2, MPMV) is used to reconstitute HIV-1's NCTE, the hybrid produces transcripts and infectious virions (Bray (1994) *Proc. Nail. Acad. Sci. USA* 91:1256–1260; Tabernero (1996) *J. Virol.* 70:5998–6011; Zolotukhin (1994) *J. Virol.* 68:7944–7952). Significantly, these hybrids produce lower levels of transcript and productive virion than seen with wild-type HIV-1.

It was surprisingly found that the novel PRE of the invention can functionally replace the NCTE of HIV-1, or "RRE." It was discovered that when PRE is used in place of RRE to construct an HIV-1 hybrid clone, a slower growing virus results. Significantly, while capable of producing infectious virions in viva, this HIV-1 hybrid (a PRE-containing RRE-negative recombinant virus) has lower replicative activity than wild-type virus, resulting in an attenuated HIV-1 strain. The level of attenuation can be quantitated using in vitro or in vivo assays, such as determining the amount of HIV-1 $p24^{gag}$ synthesized by hybrid viruses. For example, PRE-containing HIV-1 hybrids can be used to infect tissue culture cells or activated human peripheral blood mononuclear cells (huPBMCs) in vitro. When the PRE-containing hybrid HIV-1 virus infects activated huPBMCs, the level of expression of HIV-1 $p24^{gag}$ is between about 50 fold and about 200 fold less than levels of $p_{24}^{gag}$ expression when HIV-1 wild type virus, utilizing wild-type NCTE (i.e., RRE), infects activated huPBMCs.

The efficacy of the PRE-recombinant hybrid as an attenuating agent in HIV-1 infection and AIDS pathogenesis can be demonstrated using functionally analogous NCTEs, such as the SRV-1 CTE. Recombinant, hybrid HIV-1 in which NCTE from SRV-1 (termed "CTF") functionally replaces wild-type HIV-1 NCTE ("RRE") are functionally analogous to hybrid HIV-1 clones whose RRE is replaced by the PRE of the invention. PRE-hybrid and SRV-1 CTE-hybrid HIV-1 clones have approximately the same rate of propagation and infectivity, as demonstrated by the in vitro experiments discussed in Example 1. Thus, CTE attenuated HIV-1 clones can be used to demonstrate the replicative, yet non-cytopathic, effect of CTE-attenuated HIV-1 in the SCID-hu mouse model, as discussed in Example 3.

CTE(+)/RRE(−) HIV-1 clones were used to infect Thy/Liv implants, which are human thymus and liver cells transplanted in SCID-hu mice (see, e.g., Kollmann (1995) *J. Immunol.* 154:907–921). Significantly, these viruses propagated slower than both wild-type and Nef-negative HIV-1 clones. This demonstrates that they have lower replicative capacity in human lymphocytes. Furthermore, the CTE(+)/RRE(−) attenuated HIV-1 clones were not lympliocytopathic, no depletion of CD4+-bearing cells was observed. This demonstrates that slow growing HIV-1 hybrid clones utilizing exogenous NCTEs, as CTE (of SRV-1) or PRE, have an attenuated phenotype for cytotoxicity.

Analogously, when the PRE-attenuated HIV-1 of the invention infect activated human lymphocytes in vivo, they will also produce low levels of infectious virions without any lymphocytotoxic effects, i.e., levels of CD4+ T cells will not decline. Importantly, this $CTE_{IAP}$-attenuated virus will elicit an immune response in the infected, yet asymptomatic, individual.

The finding that an IAP element can be utilized in the attenuation of a retrovirus whose productive infection does not lead to loss of $CD4^+$ cells is especially unexpected in view of past findings that a human IAP has been found to be associated with $CD4^+$ T-cell immunodeficiency and dysfunction. The presence of IAP sequence has also been associated with the occurrence of carcinogenesis.

This invention also provides for a vaccine in the form of a pharmacological compositions and a kit. The pharmacological compositions can comprise a pharmaceutically acceptable carrier and the attenuated virus of the invention. The kit can comprise a container containing a vaccine formulation.

DEFINITIONS

The term "PRE" refers to post-transcriptional regulatory elements which are cis-acting nucleic acid sequences involved in the transport, stability, and translation of RNA transcripts. When PREs are functioning as part of the RNA export machinery to transport transcripts from the nucleus to the cytoplasm they are also referred to as nucleocytoplasmic transport elements, or "NCTEs." The PRE of the invention specifically refers to a family, or genus of nucleic acid sequences defined as having the following structural and functional properties: the PRE, when inserted in an HIV-1 is capable of functioning as an NCTE in place of wild-type HIV-1 NCTE (i.e., RRE). When the PRE-containing hybrid HIV-1 virus infects activated huPBMCs, the level of expression of HIV-1 $p24^{gag}$ is between about 5 fold to about 200 fold less than levels of $p24^{gag}$ expression when HIV-1 wild type virus, utilizing wild-type NCTE, infects activated huPBMCs. The PRE of the invention has at least 80% nucleic acid sequence identity to the sequence set forth in SEQ ID NO:1. In another embodiment, the PRE of the invention has at least 90% sequence identity to the sequence set forth in SEQ ID NO:1. The nucleic acid of SEQ ID NO:1 is an exemplary specie of the PRE family of the invention.

The term "nucleocytoplasmic transport element" or "NCTE" refers to cis-acting PREs which act as post-transcriptional RNA nucleo-cytoplasmic transport elements. Simian retrovirus NCTE is also referred to as "CTE." These RNA sequences typically have a high degree of secondary structure in the form of stem-loop structures, which can interact with trans-acting NCTE-binding proteins, hairpin turns, and the like. Some retroviruses, including HIV and simian retroviruses, regulate their growth through expression of their RNA using NCTEs and corresponding NCTE-binding proteins. NCTE binding with viral or cellular trans-acting NCTE-binding proteins stabilizes unspliced viral transcripts and allows interaction with cellular machinery to transport the message from the nucleus to the cytoplasm. HIV-1's NCTE is designated the "Rev-responsive element," or "RRE," (Felber (1989) *Proc. Natl. Acad. Sci. USA* 86:1495–1499); Hadzopoulou-Cladaras (1989) *J. Virol.* 63:1265–1274; Malim (1989) *Nature* 338:254–257). RRE is contained in HIV-1's gag/pol and env encoding transcript. NCTEs are further described, e.g., by Bray (1994) supra; Tabemero (1996) supra; Zolotukhin (1994) supra; Hua (1996) supra; Grate (1997) *Structure* 5:7–11.

The term "NCTE-binding protein" refers to a trans-acting polypeptide which binds to RNA NCTE sequences, typically interacting with specific secondary structures. This RNA binding protein functions with other cellular proteins in the cellular nuclear export machinery to constitutively transport message nucleic acid (mRNA) from the nucleus to the cytoplasm. An NCTE-binding protein can be encoded by endogenous cellular (cukaryotic) gene or a viral gene. HIV-1 encodes for its own specific, trans-acting NCTE-binding polypeptide, termed "Rev." Rev is further described, e.g., Hua (1996) supra; Iversen (1995) supra.

The term "HIV" refers to a lentivirus usually called "human immunodeficiency virus" which is believed to the causal agent of acquired immune deficiency syndrome, or AIDS. There are several known subtypes of HIV, including HIV-1 and HIV-2. HIV and AIDS are well described in the literature and, e.g., are further described by Gottfredsson (1997) *Front Biosci.* 2: D619–D634; Burton (1997) *Proc. Natl. Acad. Sci. USA* 94:10018–10023; Barnadas (1997) *J. Cutan. Pathol.* 24:507–510; Doms (1997) *Virology* 235:179–190; Cossarizza (1997) *AIDS* 11:1075–1088; Carpenter (1997) *JAMA* 277:1962–1969; Klein (1995) *Trends Microbiol.* 3:386–391.

The term "$p24^{gag}$ antigen" or "$p24^{gag}$" refers to the 24 kd HIV-1 polypeptide found associated with the virus' RNA genome in the core of the virion, as described, e.g., by Jones (1996) *Nat. Struct. Biol.* 3:818–820 (1996); Doe (1996) *AIDS* 10:793–794; Klenerman (1996) *AIDS* 10:348–350; Klenerman (1994) *Nature* 369:403–407. Levels of $p24^{gag}$ can be measured using any technique, such as antibody based methodologies, as described herein.

The term "Nef" refers to a 27–34 kD myristoylated protein unique to primate lentiviruses. A functional Nef gene is important for development of high viremia and AIDS. For a description of Nef, see discussion infra and, e.g., Saksela (1997) *Front Biosci.* 2: D606–D618, Greenberg (1997) *EMBO J.* 16:6964–6976; Luo (1997) *J. Virol.* 71:9531–9537; Luo (1997) *J. Virol.* 71:9524–9530; Okada (1997) *FEBS Lett.* 417:61–64.

The term "capable of functioning as a post-transcriptional RNA nucleo-cytoplasmic transport element (NCTE) in place of wild-type NCTE in a hybrid HIV-1" means that the NCTE, such as the claimed PRE, when inserted into (is part of the sequence of) an HIV-1 messenger RNA, is capable of interacting with the appropriate trans-acting polypeptides to effect the splicing and subsequent transfer of the mRNA from the nucleus to the cytoplasm. An NCTE is still considered "capable of functioning as an NCTE in place of wild-type NCTE in a hybrid HIV-1" even if it is less efficient, less accurate, or less capable, of splicing and/or transferring mRNA (of which it is a part) from the nucleus to the cytoplasm. For example, the PRE of the invention, when inserted in HIV-1, is considered capable of functioning as an NCTE in place of wild-type NCTE (RRE) in the hybrid HIV-1 even though it is less efficient than RRE; i.e., when the CTE$_{IAP}$-containing hybrid HIV-1 virus infects activated human peripheral blood mononuclear cells (huPBMCs), the level of expression of HIV-1 p24$^{gag}$ is between about 5 fold and about 200 fold less than levels of p24$^{gag}$ expression when HIV-1 wild type virus, utilizing wild-type NCTE (RRE), infects activated huPBMCs.

The term "activated" refers to a non-dormant cellular state, for example, as when a lymphocyte has been activated by an antigen, cytokine(s) or other mitogen.

The term "wild-type" refers to any form (e.g., tertiary structure), structure (e.g., secondary structure) or sequence (e.g., primary structure) of a composition, as a nucleic acid or polypeptide, as found in nature, versus structures or sequences which have been manipulated by the hand of man, i.e., recombinant nucleic acids or polypeptides.

The term "peripheral blood mononuclear cell" refers to any peripheral mononuclear white blood cell.

The term "expression cassette" refers to any recombinant expression system for the purpose of expressing a nucleic acid sequence of the invention in vitro or in vivo, constitutively or inducibly, in any cell, including prokaryotic, yeast, fungal, plant, insect or mammalian cell. The term includes linear or circular expression systems. The term includes expression systems that remain episomal or integrate into the host cell genome. The expression systems can have the ability to self-replicate or not, i.e., drive only transient expression in a cell. The term includes recombinant expression cassettes which contain only the minimum elements needed for transcription of the recombinant nucleic acid. The term also includes expression vectors.

The term "isolated," when referring to a molecule or composition, such as, for example, a polypeptide or nucleic acid, means that the molecule or composition is separated from at least one other compound, such as a protein, other nucleic acids (e.g., RNAs), or other contaminants with which it is associated in vivo or in its naturally occurring state. Thus, a polypeptide or nucleic acid is considered isolated when it has been isolated from any other component with which it is naturally associated, e.g., cell membrane, as in a cell extract. An isolated composition can, however, also be substantially pure. An isolated composition can be in a homogeneous state and can be in a dry or an aqueous solution. Purity and homogeneity can be detennined, for example, using analytical chemistry techniques such as polyacrylamide gel electrophoresis (SDS-PAGE) or high performance liquid chromatography (HPLC).

The term "polynucleotide," "nucleic acid molecule" or "nucleic acid equence" refers to a deoxyribonucleotide or ribonucleotide oligonucleotide in either single- or double-stranded form. The term encompasses nucleic acids, i.e., oligonucleotides, containing known analogues of natural nucleotides which have similar or improved binding properties, for the purposes desired, as the reference nucleic acid. The term also includes nucleic acids which are metabolized in a manner similar to naturally occurring nucleotides or at rates that are improved thereover for the purposes desired. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene(methylimino), 3'-N-carbarnate, morpholino carbamate, and peptide nucleic acids (PNAs), which contain non-ionic backbones, such as N-(2-aminoethyl) glycine units); see Oligonucleotides and Analogues, A Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) *J. Med. Chem.* 36:1923–1937; Antisense Research and Applications (1993, CRC Press) in its entirety and specifically Chapter 15, by Sanghvi. Phosphorothioate linkages are described in WO 97/03211; WO 96/39154; Mata (1997) *Toxicol Appl Pharmacol* 144:189–197. Other synthetic backbones encompasses by the tenn include methylphosphonate linkages or alternating methylphosphonate and phosphodiester linkages (Strauss-Soukup (1997) *Biochemistry* 36:8692–8698), and benzylphosphonate linkages (Samstag (1996) *Antisense Nucleic Acid Drug Dev.* 6:153–156). The term nucleic acid is used interchangeably with gene, DNA, cDNA, RNA, mRNA, oligonucleotide primer, probe and amplification product.

The term "exogenous" as in "exogenous nucleic acid" refers to a molecule (e.g., nucleic acid or polypeptide) that has been isolated, synthesized, and/or cloned, in a manner that is not found in nature, and/or introduced into and/or expressed in a cell or cellular environment other than or at levels or forms different than the cell or cellular environment in which said nucleic acid or protein can be found in nature. The term encompasses both nucleic acids originally obtained from a different organism or cell type than the cell type in which it is expressed, and also nucleic acids that are obtained from the same organism, cell, or cell line as the cell or organism in which it is expressed.

The term "endogenous" refers to a molecule, e.g., a nucleic acid or polypeptide, in a form, structure and/or sequence found in nature.

"Sequence identity" in the context of two nucleic acid or polypeptide sequences includes reference to the nucleotides (or residues) in the two sequences which are the same when aligned for maximum correspondence over a specified "comparison window." Sequence identity analysis is used to determine whether a nucleic acid is within scope of the invention. For example, to identify a specie of the PRE family of the invention. a nucleic acid must have at least 80% nucleic acid sequence identity to a sequence set forth in SEQ ID NO:1. "Sequence identity" can be analyzed by optimal alignment of sequences for comparison using any means to analyze sequence identity (homology) known in the art, e.g., by the progressive alignment method of termed "PILEUP"; by the local homology algorithm of Smith & Waterman (1981) *Adv. Appl. Math.* 2: 482; by the homology alignment algorithm of Needleman & Wunsch (1970) *J. Mol. Biol.* 48:443; by the search for similarity method of Pearson (1988) *Proc. Natl. Acad. Sci. USA* 85: 2444; by computerized implementations of these algorithms, e.g. BLAST, GAP, BESTFIT, FASTA, and TFASTA in, e.g., the Wisconsin Genetics Software Package, Genetics Computer Group, 575 Science Dr., Madison, Wis.; or, by inspection. See also Morrison (1997) *Mol. Biol. Evol.* 14:428–441, as an example of the use of PileUp, ClustalW, TreeAlign, MALIGN, and SAM sequence alignment computer programs. PILEUP uses a simplification of the progressive alignment method of Feng & Doolittle (1987) *J. Mol. Evol.* 35:351–360, and is similar to the method described by Higgins & Sharp (1989) *CABIOS* 5:151–153. The BLAST algorithm is described in Altschul (1990) *J. Mol. Biol.* 215: 403410, and BLAST software for analyses is publicly available, e.g., see National Center for Biotechnology Information at http://www.ncbi.nlm.nih.gov/. See also Corpet (1988) *Nucleic Acids Res.* 16:10881–90; Huang (1992) *Computer Applications in the Biosciences* 8:155–65; Pearson (1994) *Methods in Molec. Biol.* 24:307–31.

The term "recombinant," when used with reference to, e.g., a cell, nucleic acid, polypeptide, expression cassette or vector, refers to a material, or a material corresponding to the natural or native form of the material, that has been modified by the introduction of a new moiety or alteration of an existing moiety, or is identical thereto but produced or derived from synthetic materials. For example, recombinant cells express genes that are not found within the native (non-recombinant) form of the cell (i.e., "exogenous nucleic acids") or express native genes that are otherwise expressed at a different level, typically, under-expressed or not expressed at all. The term "recombinant means" refers to techniques where, e.g., a recombinant nucleic acid such as a cDNA encoding a protein or an antisense sequence, is inserted into an expression cassette, such as an expression vector, the resultant construct is introduced into a cell, and the cell expresses the nucleic acid, and the protein, if appropriate. "Recombinant means" also encompass the ligation of nucleic acids to coding or promoter sequences from different sources into one expression cassette or vector for expression of a fusion protein, constitutive expression of a protein, or inducible expression of a protein.

The term "test compound" refers to any synthetic or natural compound or composition. The term includes all organic and inorganic compounds; including, for example, small molecules, peptides, proteins, sugars, nucleic acids, fatty acids and the like.

The term "motif" or "domain" refers to a nucleic acid or amino acid sequence pattern, or structure, which is shared between related molecules.

The term "ameliorating" or "ameliorate" refers to any indicia of success in the treatment of a pathology or condition, including any objective or subjective parameter such as abatement, remission or diminishing of symptoms or an improvement in a patient's physical or mental well-being. Amelioration of symptoms can be based on objective or subjective parameters; including the results of a physical examination and/or a psychiatric evaluation.

The term "prophylaxis" refers to any form of prevention, delay or abatement a pathology or condition or symptom thereof, including any objective or subjective parameter.

The term "attenuated" refers to a state wherein an infectious agent, i.e., a pathogen, such as a microbial or viral agent, has a phenotype manifested by a lessened ability to grow, proliferate, or cause pathogenesis, in a host, i.e., the non-wild type, attenuated phenotype is less virulent. An infectious agent is also attenuated if its non-wild type phenotype causes a delay in the onset of symptoms or pathology in its host. For example, a PRE-attenuated HIV-1 virus is capable of replication, infection and production of infectious virions without causing clinically significant pathology in its host.

The term "immune response" in a host refers to both cellular and humoral (antibody) mediated responses to an immunogen, i.e., a compound or composition capable of eliciting an immune response. The immune response can be elicited by a foreign substance or a pathogen, and the immunogen can be a carbohydrate, a nucleic acid, a polypeptide, a lipid, or a combination of these elements.

The term "vaccine" is used in its ordinary sense, meaning an agent which is capable of eliciting a humbral and/or cell-mediated immunoprotective immune response when administered to an individual with an at least partially functioning immune system.

I. Characterization and Isolation of Nucleic Acids Encoding PRE

This invention provides for the characterization, cloning and expression of a novel NCTE, the PRE of the invention. Initially derived from murine genomic sequence, it is homologous to intracistemal A particles (IAPs). The invention also provides for novel means of expressing the PRE of the invention in vitro and in vivo. In a further embodiment, these expression systems provide a means to screen for novel NCTEs.

The invention can be practiced in conjunction with any method or protocol known in the art, which are well described in the scientific and patent literature. Therefore, only a few general techniques will be described prior to discussing specific methodologies and examples relative to the novel reagents and methods of the invention.

A. General Techniques

Methods of isolating total DNA or RNA encoding the nucleic acids of the invention are well known to those of skill in the art. Techniques for isolation, purification and manipulation of nucleic acids, genes and $CTE_{IAP}$ sequences, such as generating libraries, subcloning into expression vectors, labeling probes, DNA hybridization, and the like are described, e.g., in Sambrook, MOLECULAR CLONING: A LABORATORY MANUAL (2ND ED.), Vols. 1–3, Cold Spring Harbor Laboratory, (1989) ("Sambrook"); CURRENT PROTOCOLS IN MOLECULAR BIOLOGY, Ausubel, ed. John Wiley & Sons, Inc., New York (1997) ("Ausubel"); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, P. Tijssen, ed. Elsevier, N.Y. (1993) ("Tijssen").

The nucleic acids of this invention, whether RNA, mRNA, DNA, cDNA, genomic DNA, or a hybrid of the genetic recombinations, may be isolated from a variety of sources or may be synthesized in vitro. Nucleic acids of the invention can be expressed in transgenic animals, transformed cells, in a transformed cell lysate, or in a partially purified or a substantially pure form. Sequencing methods typically use dideoxy sequencing (Sequenase, U.S. Biochemical), however, other kits and methods are available and well known to those of skill in the art.

Nucleic acids and proteins are detected and quantified in accordance with the teachings and methods of the invention. described herein by any of a number of general means well known to those of skill in the art. These include, for example, analytical biochemical methods such as spectrophotometry, radiography, electrophoresis, capillary electrophoresis, high performance liquid chromatography (HPLC), thin layer chromatography (TLC), and hyperdiffusion chromatography, various immunological methods, such as fluid or gel precipitin reactions, immunodiffusion (single or double), immunoelectrophoresis, radioimmunoassays (RIAs), enzyme-linked immunosorbent assays (ELISAs), immuno-fluorescent assays, and the like, Southern analysis, Northern analysis, Dot-blot analysis, gel electrophoresis, RT-PCR, quantitative PCR, other nucleic acid or target or signal amplification methods, radiolabeling, scintillation counting, and affinity chromatography, to name only a few.

B. Identification, Synthesis and Purification of PRE Nucleic Acids

The invention provides means to identify, synthesize and purify PRE of the invention and its alleles, isoforms and polymorphisms.

1. Preparation and Screening of DNA Libraries

There are numerous methods for isolating the DNA sequences encoding the PRE of the invention. For example, DNA can be isolated from a genomic or cDNA library using labeled oligonucleotide probes having sequences complementary to the sequences or subsequences disclosed herein, such as SEQ ID NO:1. Such probes can be used directly in hybridization assays to isolate DNA encoding PRE isoforms and polymorphisms. Alternatively, probes can be designed for use in amplification techniques, such as, e.g., PCR. PRE nucleic acid can be identified and produced using such amplification methods, as described herein.

To prepare a cDNA library, mRNA is isolated, reverse transcribed from the mRNA according to procedures well known in the art The cDNA can be inserted into any expression cassette or vector. The cassettes or vectors are transfected into a recombinant host for propagation, screening and cloning. Methods for making and screening cDNA libraries are well known. See, e.g., Gubler (1983) Gene 25:263–269, Sambrook, Ausubel.

To make a genomic library, total DNA is extracted and purified by well-known methods (see, e.g., Sambrook). DNA of appropriate size is produced by known methods, such as mechanical shearing or enzymatic digestion, to yield DNA fragments, e.g., of about 12 to 20 kb. The fragments are then separated, as for example, by gradient centrifugation, or gel electrophoresis, from undesired sizes. Selected fragments can be inserted in bacteriophage, expression cassettes, or other vectors. Recombinant phage can be analyzed by plaque hybridization described, e.g., in Benton (1977) Science 196: 180; Chen (1997) Methods Mol Biol 62:199–206. Colony hybridization is generally described in, e.g., Grunstein (1975) Proc. Natl. Acad. Sci. USA 72:3961–3965; Yoshioka (1997) J. Immunol Methods 201:145–155; Palkova (1996) Biotechniques 21:982.

DNA encoding an PRE can be identified in either cDNA or genomic libraries by hybridization with nucleic acid probes of the invention. For example, a probe containing 10 to 20 to 50 or more contiguous nucleotides of SEQ ID NO:1 is used in Southern blots to identify a PRE of the invention. Once identified, these DNA regions are isolated by standard methods familiar to those of skill in the art. Alternatively, RNA may be identified by hybridization to nucleic acid probes in Northern blots or other formats; see, e.g., Sambrook, Ausubel, for general procedures.

Oligonucleotides for use as, e.g., probes, templates for further amplification, and the like, can be chemically synthesized, as described below. Synthetic nucleic acids, including oligonucleotide probes and primers, PRE sequences, and the like, can be prepared by a variety of solution or solid phase methods. Detailed descriptions of the procedures for solid phase synthesis of nucleic acids by phosphite-triester, phosphotriester, and H-phosphonate chemistries are widely available. For example, the solid phase pliosphoramidite triester method of Beaucage and Carruthers using an automated synthesizer is described in Itakura, U.S. Pat. No. 4,401,796; Carruthers, U.S. Pat. Nos. 4,458,066 and 4,500,707; Carruthers (1982) Genetic Engineering 4:1–17. See also Needham-VanDevanter (1984) Nucleic Acids Res. 12:6159–6168; Beigelman (1995) Nucleic Acids Res 23: 3989–3994; OLIGONUCLEOTIDE SYNTHESIS: A PRACTICAL APPROACH, Gait (ed.), IRL Press, Washington D.C. (1984), see Jones, chapt 2, Atkinson, chapt 3, and Sproat, chapt 4; Froehler (1986) Tetrahedron Lett. 27:469–472; Froehler, Nucleic Acids Res. 14:5399–5407 (1986); Sinha (1983) Tetrahedron Lett. 24:5843–5846; and Sinha (1984) Nucl. Acids Res. 12:4539–4557. Methods to purify oligonucleotides include native acrylamide gel electrophoresis, anion-exchange HPLC, as described in Pearson (1983) J. Chrom. 255:137–149. The sequence of the synthetic oligonucleotide can be verified using any chemical degradation method, e.g., Maxam (1980) Methods in Enzymology 65:499–560, Xiao (1996) Antisense Nucleic Acid Drug Dev 6:247–258; for solid-phase chemical degradation, Rosenthal (1987) Nucleic Acids Symp Ser 18:249–252.

2. Amplification of Nucleic Acids

The present invention provides oligonucleotide primers and probes that can hybridize specifically to and amplify nucleic acids having PRE sequences. Such reagents can be used to identify further PRE species, such as polymorphisms alleles and other variations. For illustrative purposes, exemplary PCR primers and amplification methods are described herein.

For amplification of PRE, nucleic acid conserved amongst different PRE species are preferred reagents for use as hybridization and amplification probes to identify and isolate additional species from various organisms. Oligonucleotides can be used to identify and detect additional PRE species using a variety of hybridization techniques and conditions. Suitable amplification methods include, e.g., polymerase chain reaction, PCR (PCR PROTOCOLS, A GUIDE TO METHODS AND APPLICATIONS, ed. Innis, Academic Press, N.Y. (1990) and PCR STRATEGIES (1995), ed. Innis, Academic Press, Inc., N.Y. (Innis)), ligase chain reaction (LCR) (Wu (1989) Genomics 4:560; Landegren (1988) Science 241:1077; Barringer (1990) Gene 89:117); transcription amplification (Kwoh (1989) Proc. Natl. Acad. Sci. USA 86:1173); self-sustained sequence replication (Guatelli (1990) Proc. Natl. Acad. Sci. USA, 87:1874); Q Beta replicase amplification and other RNA polymerase mediated techniques (e.g., NASBA, Cangene, Mississauga, Ontario). See Berger (1987) Methods Enzymol. 152:307–316, Sambrook, Ausubel, Mullis (1987) U.S. Pat. Nos. 4,683,195 and 4,683,202; Amheim (1990) C&EN 36–47; Lomell J. Clin. Chem., 35:1826 (1989); Van Brunt, Biotechnology, 8:291–294 (1990); Wu (1989) Gene 4:560; Sooknanan (1995) Biotechnology 13:563–564. Methods for cloning in vitro amplified nucleic acids are described in Wallace, U.S. Pat. No. 5,426,039.

The invention provides for amplification and manipulation or detection of the products from each of the above methods to prepare DNA encoding PRE nucleic acid. In PCR techniques, oligonucleotide primers complementary to the two borders of the DNA region to be amplified are synthesized and used (see, Innis). PCR can be used in a variety of protocols to amplify, identify, quantify, isolate and manipulate nucleic acids encoding PRE. In these protocols, primers and probes for amplification and hybridization are generated that comprise all or any portion of the DNA sequences listed herein An illustrative primer pair that can amplify the PRE of the invention under appropriate conditions includes an oligonucleotide incorporating about the first twenty or thirty nucleic acids of the exemplary PRE of the invention, i.e., 5'-GTGGGGTGCG AGGCTAAGCA CTGCACAGAG-3', the 5' thirty nucleotides of SEQ ID NO:1; and, an oligonucleotide complementary to the 3' twenty to thirty nucleic acids, i.e., 5'-AAGCAAGCCT CATGGGTGAA GGTAGAGGAC-3' (SEQ ID NO:2).

PCR-amplified sequences can also be labeled and used as detectable oligonucleotide probes, but such nucleic acid probes can be generated using any synthetic or other technique well known in the art, as described above. The labeled amplified DNA or other oligonucleotide or nucleic acid of the invention can be used as probes to further identify and isolate PRE species from various cDNA or genomic libraries.

Another useful means of obtaining nucleic acids of the invention, such as large genomic clones, is to screen YAC, BAC or P1 genomic libraries. BACs, bacterial artificial chromosomes, are vectors that can contain 120+Kb inserts. BACs are based on the E. coli F factor plasmid system and simple to manipulate and purify in microgram quantities.

Because BAC plasmids are kept at one to two copies per cell, the problems of rearrangement observed with YACs, which can also be employed in the present methods, are eliminated. BAC vectors can include marker genes for luciferase and green fluorescent protein (GFP). (Baker (1997) *Nucleic Acids Res* 25:1950–1956). Yeast artificial chromosomes, or YACS, can also be used for contain inserts ranging in size from 80 to 700 kb, see, e.g., Tucker (1997) *Gene* 199:25–30; Adam (1997) *Plant J.* 11:1349–1358. P1 is a bacteriophage that infects *E. coli* that can contain 75–100 Kb DNA inserts (Mejia (1997) *Genome Res* 7:179–186; Ioannou (1994) *Nat Genet* 6:84–89), and are screened in much the same way as lambda libraries.

3. Cloning PRE-Encoding Inserts

The invention also provides PRE-encoding expression cassettes and vectors to produce large quantities of full or partial length PRE nucleic acid. The expression vectors and cassettes include, e.g., those used in bacterial, yeast, plant, insect, in vitro, or mammalian systems. For example, generation of PRE in this manner is useful for assaying for PRE activity modulators, analysis of the activity of newly isolated species of PRE, identifying and isolating compounds which specifically associate with PRE, such as binding proteins, or analysis of the activity of PRE which has been site-specifically mutated. The nucleic acids of the invention can also be used as immunogens, as a few examples, see, e.g., Radic (1994) *Annu. Rev. Immunol.* 12:487–520; Cabral (1997) *Curr. Opin. Rheumatol.* 9:387–392; Pisetsky (1997) *Methods* 11:55–61; Marion (1997) *Methods* 11:3–11, for general discussion on anti-DNA antibodies; for discussion on generation of anti-RNA antibodies using combinatorial phage display libraries see Marchbank (1995) *Nucleic Acids Symp. Ser.* 33:120–122.

There are several well-known methods of introducing nucleic acids into bacterial and other cells, a process often called "transforming," any of which may be used in the methods of the present invention (see, e.g., Sambrook). Techniques for transforming a wide variety of animal and plant cells are well known and described in the technical and scientific literature. See, e.g., Weising (1988) *Ann. Rev. Genet.* 22:421–477, for plant cells and Sambrook for animal and bacterial cells.

4. Sequencing of PRE-Encoding Nucleic Acid

Sequencing of newly isolated DNA will identify and characterize PRE-encoding nucleic acid of the invention. Sequencing of isolated PRE-encoding nucleic acid can be used to identify, in addition to functional criteria, new PRE-encoding species or allelic variations. Secondary structures can be identified. For example, in terms of primary sequence criteria, a nucleic acid is a PRE specie within the scope of the claimed invention if its sequence has least 80% nucleic acid sequence identity to SEQ ID NO:1.

PRE-encoding nucleic acid sequences can be sequenced as inserts in vectors, as inserts released and isolated from the vectors or in any of a variety of other forms (i.e., as amplification products). PRE-encoding inserts can be released from the vectors by restriction enzymes or amplified by PCR or transcribed by a polymerase. For sequencing of the inserts to identify full length PRE coding sequences, primers based on the N- or C-terminus, or based on insertion points in the original phage or other vector, can be used. Additional primers can be synthesized to provide overlapping sequences.

A variety of nucleic acid sequencing techniques are well known and described in the scientific and patent literature, e.g., see Rosenthal (1987) supra; Arlinghaus (1997) *Anal. Chem.* 69:3747–3753, for use of biosensor chips for sequencing; Pastinen (1996) *Clin. Chem.* 42:1391–1397; Nyren (1993) *Anal Biochem.* 208:171–175.

5. Nucleic Acid Hybridization Techniques

The hybridization techniques disclosed herein can be utilized to identify, isolate and characterize amplicon-encoding nucleic acid of the invention, including different isoforms, alleles and polymorphisms of such sequences. A variety of methods for specific DNA and RNA measurement using nucleic acid hybridization techniques are known to those of skill in the art. See. e.g., NUCLEIC ACID HYBRIDIZATION, A PRACTICAL APPROACH, Ed. Hames, B. D. and Higgins, S. J., IRL Press, 1985; Sambrook.

One method for evaluating the presence or absence of DNA encoding PRE of the invention in a sample involves a Southern transfer. Briefly, the digested bacterial genomic DNA is run on agarose slab gels in buffer and transferred to membranes. Hybridization is carried out using nucleic acid probes. The nucleic acid probes can be designed based on conserved nucleic acid sequences. Preferably nucleic acid probes are 20 bases or longer in length (see, e.g., Sambrook for methods of selecting nucleic acid probe sequences for use in nucleic acid hybridization). Visualization of the hybridized portions allows the qualitative determination of the presence or absence of PRE DNA.

Similarly, a Northern transfer can be used for the detection of RNA containing PRE sequences. For example, RNA is isolated from a given cell sample using an acid guanidinium-phenol-chloroform extraction method. The RNA is then electrophoresed to separate different species and transferred from the gel to a nitrocellulose membrane. As with the Southern transfers, labeled probes or PCR can be used to identify the presence or absence of PRE nucleic acid.

Sandwich assays are commercially useful hybridization assays for detecting or isolating protein or nucleic acid. Such assays utilize a "capture" nucleic acid or protein that is often covalently immobilized to a solid support and a labeled "signal" nucleic acid, typically in solution. A clinical or other sample provides the target nucleic acid or protein. The "capture" nucleic acid or protein and "signal" nucleic acid or protein hybridize with or bind to the target nucleic acid or protein to form a "sandwich" hybridization complex. To be effective, the signal nucleic acid or protein cannot hybridize or bind substantially with the capture nucleic acid or protein.

Typically, oligonucleotide probes are labeled signal nucleic acids that are used to detect hybridization. Complementary probe nucleic acids or signal nucleic acids may be labeled by any one of several methods typically used to detect the presence of hybridized polynucleotides. Methods of detection can use labels for autoradiography or autofluorography, such as $^3$H, $^{125}$I, $^{35}$S, $^{14}$C, or $^{32}$P-labeled probes or the like (see definition of label, above). Other labels include ligands which bind to labeled antibodies, fluorophores, chemiluminescent agents, enzymes, and antibodies which can serve as specific binding pair members for a labeled ligand.

Detection of a hybridization complex may require the binding of a signal generating complex to a duplex of target and probe polynucleotides or nucleic acids. Typically, such binding occurs through ligand and anti-ligand interactions as between a ligand-conjugated probe and an anti-ligand conjugated with a signal, i.e., antibody-antigen or complementary nucleic acid binding. The label may also allow indirect detection of the hybridization complex. For example, where the label is a hapten or antigen, the sample can be detected by using antibodies. In these systems, a signal is generated by attaching fluorescent or enzymatic molecules to the antibodies or, in some cases, by attachment of a radioactive label. The sensitivity of the hybridization assays may be enhanced through use of a target nucleic acid or signal amplification system which multiplies the target nucleic acid or signal being detected. These systems can be used to directly identify PRE variations, polymorphisms, or mutated sequences. Alternatively, the specific sequences can be amplified using, e.g., generic PCR primers, and the amplified target region later probed or sequenced to identify a specific sequence indicative of the variant, polymorphism or mutation.

Nucleic acid hybridization assays for the detection of isoforms, mutations and for sequencing can also be performed in an array-based format. Arrays are a multiplicity of different "probe" or "target" nucleic acids (or other compounds) are hybridized against a target nucleic acid. In this manner a large number of different hybridization reactions can be run essentially "in parallel". This provides rapid, essentially simultaneous, evaluation of a wide number of reactants. Methods of performing hybridization reactions for detection and sequencing in array based formats are well known, e.g., Pastinen (1997) *Genome Res.* 7:606–614; Jackson (1996) *Nature Biotechnology* 14:1685; Chee (1995) *Science* 274:610.

An alternative means for determining the level of expression of a gene is in situ hybridization. In situ hybridization assays are well known (e.g., Angerer (1987) *Methods Enzymol* 152:649). In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence. The probes are typically labeled, i.e., with radio-isotopes or fluorescent reporters. Another well-known in situ hybridization technique is the so-called fluorescence in situ hybridization (FISH), see, e.g., Macechko (1997) *J. Histochem. Cytochem.* 45:359–363; Raap (1995) *Hum. Mol. Genet.* 4:529–534.

The sensitivity of the hybridization assays may be enhanced through use of a nucleic acid amplification system which multiplies the target nucleic acid being detected. Alternatively, the select sequences can be generally amplified using nonspecific PCR primers and the amplified target region later probed for a specific sequence indicative of a mutation.

Oligonucleotides for use as probes, e.g., in vitro amplification methods, as gene probes in diagnostic methods, or as inhibitor components (see below) are typically synthesized chemically; e.g., such as by the solid phase phosphoramidite triester method described by Beaucage and Caruthers, supra, or, using an automated synthesizer, as described in Needham-VanDevanter, supra. Purification of oligonucleotides, where necessary, is typically performed by native acrylamide gel electrophoresis or by anion-exchange HPLC as described in Pearson and Regnier. The sequence of the synthetic oligonucleotides can be verified using the chemical degradation method of Maxam and Gilbert (Maxam (1980) supra).

It will be appreciated that nucleic acid hybridization assays can also be performed in an array-based format. In this approach, arrays bearing a multiplicity of different "probe" nucleic acids are hybridized against a target nucleic acid. In this manner a large number of different hybridization reactions can be run essentially "in parallel". This provides rapid, essentially simultaneous, evaluation of a wide number of reactants. Methods of performing hybridization reactions in array based formats are well known to those of skill in the art (see. e.g., Jackson (1996) *Nature Biotechnol.* 14:1685, and Chee (1995) *Science* 274:610).

6. Sequence Comparison Analysis

PRE-encoding nucleic acid sequences of the invention include both genes and gene transcription products (mRNA) identified and characterized by analysis of PRE sequences. Optimal alignment of sequences for comparison can be conducted as described herein (see definitions). Sequence identity analysis can also supplement functional analysis to determine whether a nucleic acid is within scope of the invention. For example, in other embodiments, a PRE sequence of the invention has at least 80% nucleic acid sequence identity to SEQ ID NO:1, has at least 90% nucleic acid sequence identity to the sequence as set forth in SEQ ID NO:1, or can comprise a sequence as set forth in SEQ ID NO:1. Publicly available nucleic acid databanks can be searched for sequence identity (homology) to the exemplary SEQ ID NO:1 PRE of the invention to identify additional members of the PRE family of the invention. Any of the programs described herein (see definitions) can be used to identify PRE family members.

For example, the program PileUp was used to identify a PRE of the invention. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle (1987) supra; see also the method of Higgins & Sharp (1989) supra. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps. See also Morrison (1997) supra, for the use of PILEUP.

PileUP was used with the parameters: symbol comparison table: GenRunData:pileupdna.cmp, GapWeight:2, GapLength Weight:1 (see Example 1) to identify a PRE of the invention. The following PRE sequence thus identified is within the scope of the invention, having about 83% sequence identity to SEQ ID NO:1: AGGAGTTGCA AGGCTAAGC X ACTGCACAGG AGAGG X TCTG CGG XX TATAA CGACTTTCTC CTGGGAGATA AGTCATCTTG CATGAAGGTT CTATG X TCAT, where X is any nucleotide (SEQ ID NO:6).

The BLAST program can also be used to identify a PRE family member by sequence identity. For example, BLAST can uses as defaults a wordlength (W) of 11, the BLOSUM62 scoring matrix (see Henikoff (1992) *Proc. Natl. Acad. Sci. USA* 89:10915–10919) alignments (B) of 50, expectation (E) of 10, M=5, N=−4, and a comparison of both strands. The term BLAST refers to the BLAST algorithm which performs a statistical analysis of the similarity between two sequences; see, e.g., Karlin (1993) *Proc. Natl. Acad. Sci. USA* 90:5873–5787. One measure of similarity provided by the BLAST algorithm is the smallest sum probability (P(N)), which provides an indication of the probability by which a match between two nucleotide or amino acid sequences would occur by chance.

II. Functional Analyses: Measuring Levels of Viral Expression

Functional analysis can supplement sequence identity analysis to determine whether a nucleic acid is within scope of the invention and to characterize the level of attenuation effected by the PRE. For example, cell cultures or activated PMBCs can be infected in vitro with PRE-containing recombinant viruses of the invention. The level of attenuation can be determined by measuring the amounts of total virion or virus product produced. Viral products include polypeptides (e.g., $p24^{gag}$) and transcription products (mRNA message). Viral polypeptides can can be quantitated by e.g., antibody based assays, enzymatic assays, and the like. A variety of standard protocols for detecting and measuring the expression of proteins using either polyclonal or monoclonal antibodies specific for the protein are known in the art. Examples include enzyme-linked immunosorbent assay (ELISA), radioimmunoassay (RIA) and fluorescent activated cell sorting (FACS). These and other assays are described, e.g., in Hampton et al., *Serological Methods a Laboratory Manual*, APS Press, St Paul Minn., 1990); Maddox (1983) *J. Exp. Med.* 158:121 1); Coligan, CURRENT PROTOCOLS IN IMMUNOLOGY, Wiley/Greene, NY (1991); Stites (eds.) BASIC AND CLINICAL IMMUNOLOGY (7th ed.) Lange Medical Publications, Los Altos, Calif.; Goding, MONOCLONAL ANTIBODIES: PRINCIPLES AND PRACTICE (2d ed.) Academic Press, New York, N.Y. (1986). Polypeptides can be isolated and then quantitated. Protein concentrations can be determined using any technique, e.g., as in Bradford (1976) *Anal. Biochem.* 72:248–257. Nucleic acid products can be quantitated by, e.g., hybridization, PCR, and the like, as described herein.

When the PRE-containing hybrid HIV-1 virus infects activated huPBMCs, the level of expression of HIV-1 $p24^{gag}$ is between about 5 fold and about 200 fold less than levels of $p24^{gag}$ expression when HIV-1 wild type virus infects activated huPBMCs. Levels of $p24^{gag}$ expression can be measured by any means known in the art, such as, e.g., antibody based assays, as ELISA assays. For example, virus propagation can be monitored over time using a $p24^{gag}$ antigen capture ELISA assay. A commercial ELISA assay (Cellular Products, Buffalo, N.Y.) used according to manufacturer's instructions or any $p24^{gag}$ antigen capture assay using techniques well known in the art can be used (see, e.g., Zolotukhin (1994) supra; Van Doornum (1998) *J. Med. Virol.* 54:285–290; Hashida (1998) *J. Clin. Lab. Anal.* 12:115–120; Palenzuela (1997) *J. Immunol. Methods* 208:43–48).

III. Mutagenesis of PRE Nucleic Acid

The invention also provides for PRE nucleic acid that have been modified in a site-specific manner to modify, add to, or delete some or all functions. For example, specific base pairs can be modified to alter, increase or decrease the affinity of NCTE binding proteins, thus modifying the relative level of attenuation. Alternatively, modifications can change the stability of the secondary structure of the nucleic acid. Base pair changes can augment expression of the nucleic acid in a cell, such as a bacteria.

Site-specific mutations can be introduced into PRE-encoding nucleic acid by a variety of conventional techniques, well described in the scientific and patent literature. Illustrative examples include: site-directed mutagenesis by overlap extension polymerase chain reaction (OE-PCR), as in Urban (1997) *Nucleic Acids Res.* 25:2227–2228; Ke (1997) *Nucleic Acids Res* 25:3371–3372; Chattopadhyay (1997) *Biotechniques* 22:1054–1056, describing PCR-based site-directed mutagenesis "megaprimer" method; Bohnsack (1997) *Mol. Biotechnol.* 7:181–188; Ailenberg (1997) *Biotechniques* 22:624–626, describing site-directed mutagenesis using a PCR-based staggered re-annealing method without restriction enzymes; and Nicolas (1997) *Biotechniques* 22:430–434, describing site-directed mutagenesis using long primer-unique site elimination and exonuclease III.

Modified PRE of the invention can be further produced by chemical modification methods, see, e.g., Belousov (1997) *Nucleic Acids Res.* 25:3440–3444; Frenkel (1995) *Free Radic. Biol. Med.* 19:373–380; Blommers (1994) *Biochemistry* 33:7886–7896.

IV. Expression of PRE Nucleic Acid

The invention provides for methods and reagents the expression of novel PRE nucleic of the invention in any prokaryotic, eukaryotic, yeast, fungal, plant, insect, human or animal cell. Antisense, in addition to sense, sequences are provided. To create cell-based and in vitro assay systems to screen for novel NCTEs using PRE of the invention, a variety of in vivo and in vitro expression systems are provided.

A. Vectors and Transcriptional Control Elements

The invention provides for methods and reagents for expressing the novel PRE of the invention as sense or antisense coding sequences, or in other constructs, such as ribozymes. Other embodiments of the invention provide methods and reagents for identifying, isolating and using PRE to identify and isolate trans-acting NCTE binding proteins. After the coding region of a PRE has been identified, it can be expressed by operably linking the coding region to transcriptional regulatory elements, such as promoters and enhancers. These sequences have characteristic subsequences, for instance, promoter sequence elements typically include the TATA box consensus sequence (TATAAT), which is usually 20 to 30 base pairs upstream of the transcription start site. Promoters can be tissue-specific or not, constitutive or inducible. Promoters that drive expression continuously under physiological conditions are referred to herein as "constitutive" promoters and are active under most environmental conditions and states of development or cell differentiation. Typical expression systems, such as expression cassettes and vectors, also contain transcription and translation terminators, transcription and translation initiation sequences. Generic expression cassettes typically contain at least one independent terminator sequence, sequences permitting replication of the cassette in eukaryotes, or prokaryotes, or both, (e.g., shuttle vectors) and selection markers for both prokaryotic and eukaryotic systems. See, e.g., Roberts (1987) *Nature* 328:731; Berger (1987) supra; Schneider (1995) *Protein Expr. Purif.* 6435:10; Sambrook and Ausubel. Product information from manufacturers of biological reagents and experimental equipment also provide biological methodologies, such as, e.g., the SIGMA Chemical Company (Saint Louis, Mo.), Pharmacia Biotech (Piscataway, N.J.), Clontech Laboratories, Inc. (Palo Alto, Calif.), Aldrich Chemical Company (Milwaukee, Wis.), GIBCO BRL Life Technologies, Inc. (Gaithersburg, Md.), Fluka Chemica-Biochemika Analytika (Fluka Chemie A G, Buchs, Switzerland). The promoters and vectors used in this invention can be isolated from natural sources, obtained from such sources as ATCC or GenBank libraries, or prepared by synthetic methods, as described herein.

The PRE sequences of the invention can be expressed in cassettes or vectors which are transiently expressed in cells using, e.g., episomal vectors such as vaccinia virus, see Cooper (1997) *Proc Natl Acad Sci USA* 94:6450–6455. They can include sequences coding for episomal maintenance and replication such that integration into the host genome is not required. Alternatively, PRE coding sequences can be inserted into the host cell genome becoming an integral part of the host chromosomal DNA, using, e.g., retroviral vectors such as SIV or HIV, see e.g., Naldini (1996) *Science* 272:263–267. Expression vectors can contain selection markers that confer a selectable phenotype on transformed cells. For example, a marker may encode antibiotic resistance, as to chloramphenicol, kanamycin, G418, bleomycin or hygromycin, to permit selection of those cells transformed with the desired DNA sequences, see, e.g., Blondelet-Rouault (1997) *Gene* 190:315–317. Because selectable marker genes conferring resistance to substrates like neomycin or hygromycin can only be utilized in tissue culture, chemoresistance genes are also used as selectable markers in vitro and in vivo. Various target cells are rendered resistant to anticancer drugs by transfer of chemoresistance genes encoding, e.g., P-glycoprotein, multidrug resistance-associated protein-transporter, dihydrofolate reductase, glutathione -S-transferase, O 6-alkylguanine DNA alkyltransferase, or aldehyde reductase (Licht (1997) *Stem Cells* 15:104–111). Illustrative vectors incorporating PRE of the invention include, e.g., adenovirus-based vectors (Cantwell (1996) *Blood* 88:4676–4683; Ohashi (1997) *Proc Natl Acad Sci USA* 94:1287–1292), Epstein-Barr virus-based vectors (Mazda (1997) *J Immunol Methods* 204:143–151), adenovirus-associated virus vectors, Sindbis virus vectors (Strong (1997) *Gene Ther.* 4: 624–627), Herpes simplex virus vectors (Kennedy (1997) *Brain* 120: 1245–1259) and retroviral vectors (Schubert (1997) *Curr Eye Res* 16:656–662). Epstein-Barr virus episomal vectors (Horlick (1997) *Protein Expr. Purif.* 9:301–308, and plasmid DNA (Lowrie (1997) *Vaccine* 15: 834–838); all of which can be used to express the nucleic acids of the invention in vivo or ex vivo V. Inhibiting Expression of PRE Nucleic Acid The invention further provides for nucleic acids which can inhibit the expression or function of PRE nucleic acids. These inhibitory nucleic acids are typically complementary to, i.e., are antisense sequences to, the PRE of the invention. Expression of inhibitory nucleic acid sequences can be used to completely inhibit or further depress the replicative potential of an attenuated virus. For example, a hybrid HIV-1 virus can be designed to express inhibitory nucleic acid sequence under the control of an inducible promoter. Thus, if desired, after administration of a PRE-attenuated viral vaccine, the expression and function of the sense PRE, and thus the replicative potential of the virus, can be down-regulated or turned off.

The inhibition can be effected through the targeting of genomic DNA or messenger RNA. The transcription or function of targeted nucleic acid can be inhibited, for example, by hybridization and/or cleavage. One particularly useful set of inhibitors provided by the present invention includes oligonucleotides which are able to either bind PRE gene or message, in either case preventing or inhibiting the production, splicing, transport, or function of viral message. The association can be though sequence specific hybridization. Another useful class of inhibitors includes oligonucleotides which cause inactivation or cleavage of PRE-containing message. The oligonucleotide can have enzyme activity which causes such cleavage, such as ribozymes. The oligonucleotide can be chemically modified or conjugated to an enzyme or composition capable of cleaving the complementary nucleic acid. One may screen a pool of many different such oligonucleotides for those with the desired activity.

1. Antisense Oligonucleotides

The invention provides for with antisense oligonucleotides capable of binding PREcontaining message to inhibit or further depress the replicative potential of a PRE-containing attenuated virus. Strategies for designing antisense oligonucleotides are well described in the scientific and patent literature, and the skilled artisan can design such PRE complementary oligonucleotides using the novel reagents of the invention. In some situations, naturally occurring nucleic acids used as antisense oligonucleotides may need to be relatively long (18 to 40 nucleotides) and present at high concentrations. A wide variety of synthetic, non-naturally occurring nucleotide and nucleic acid analogues are known which can address this potential problem. For example, peptide nucleic acids (PNAs) containing non-ionic backbones, such as N-(2-aminoethyl) glycine units can be used. Antisense oligonucleotides having phosphorothioate linkages can also be used, as described in WO 97/03211; WO 96/39154; Mata (1997) *Toxicol Appl Pharmacol* 144:189–197; Antisense Therapeutics, ed. Agrawal (Humana Press, Totowa, N.J., 1996). Antisense oligonucleotides having synthetic DNA backbone analogues provided by the invention can also include phosphoro-dithioate, methylphosphonate, phosphoramidate, alkyl phosphotriester, sulfamate, 3'-thioacetal, methylene (methylimino), 3'-N-carbamate, and morpholino carbamate nucleic acids, as described above.

Combinatorial chemistry methodology can be used to create vast numbers of oligonucleotides that can be rapidly screened for specific oligonucleotides that have appropriate binding affinities and specificities toward any target, such as the sense and antisense PRE sequences of the invention (for general background information, see, e.g., Gold (1995) *J. of Biol. Chem.* 270:13581–13584).

2. Inhibitory Ribozymes

The invention provides for with ribozymes capable of targeting PRE-containing message to inhibit, e.g., the splicing, transport, protein-binding capacity, or translation of viral mRNA, for further attenuating a PRE-containing hybrid virus. Strategies for designing ribozynies and selecting PRE antisense sequence for targeting are well described in the scientific and patent literature, and the skilled artisan can design such ribozynies using the novel reagents of the invention. Ribozymes act by binding to a target RNA through the target RNA binding portion of a ribozyme which is held in close proximity to an enzymatic portion of the RNA that cleaves the target RNA. Thus, the ribozyme recognizes and binds a target RNA through complementary base-pairing, and once bound to the correct site, acts enzymatically to cleave and inactivate the target RNA. For example, ribozyme cleavage of PRE-containing message would prevent binding to NCTE binding protein, thus preventing subsequent transport of the message to the cytoplasm. After a ribozyme has bound and cleaved its RNA target, it is typically released from that RNA and so can bind and cleave new targets repeatedly.

The effective concentration of ribozyme necessary to effect a therapeutic treatment can be lower than that of an antisense oligonucleotide. This potential advantage reflects the ability of the ribozyme to act enzymatically. Thus, a single ribozyme molecule is able to cleave many molecules of target RNA. In addition, a ribozyme is typically a highly specific inhibitor, with the specificity of inhibition depending not only on the base pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base pairing. Thus, the specificity of action of a ribozyine can be greater than that of antisense oligonucleotide binding the same RNA site.

The enzymatic ribozyme RNA molecule can be formed in a hammerhead motif, but may also be formed in the motif of a hairpin, hepatitis delta virus, group I intron or RNaseP-like RNA (in association with an RNA guide sequence). Examples of such hammerhead motifs are described by Rossi (1992) *Aids Research and Human Retroviruses* 8:183; hairpin motifs by Hampel (1989) *Biochemistry* 28:4929, and Hampel (1990) *Nuc. Acids Res.* 18:299; the hepatitis delta virus motif by Perrotta (1992) *Biochemistry* 31:16; the RNaseP motif by Guerrier-Takada (1983) *Cell* 35:849; and the group I intron by Cech U.S. Pat. No. 4,987,071. The recitation of these specific motifs is not intended to be limiting; those skilled in the art will recognize that an enzymatic RNA molecule of this invention has a specific substrate binding site complementary to one or more of the target gene RNA regions, and has nucleotide sequence within or surrounding that substrate binding site which imparts an RNA cleaving activity to the molecule.

VI. Construction of Attenuated Virus and Viral Vaccine

The invention provides for an attenuated retrovirus and vaccine comprising the PRE of the invention. One means to genetically engineer a wild-type, virulent virus to a hybrid, attenuated virus involves constructing a virus which either lacks or has a non-functional endogenous post-transcriptional RNA nucleo-cytoplasmic transport elements (NCTEs). The endogenous NCTE is subsequently replaced by the exogenous NCTE of the invention which functions less efficiently in vivo than its wild-type counterpart, thus effecting the attenuation. For example, insertion of the PRE of the invention in a RRE(−) and/or Rev(−) HIV-1 creates a slower growing, "attenuated" hybrid virus. This level of attenuation can be measured. When the PRE-containing hybrid HIV-1 virus infects activated huPBMCs, the level of expression of HIV-1 $p24^{gag}$ is between about 5 fold and about 200 fold less than levels of $p24^{gag}$ expression when HIV-1 wild type virus, utilizing wild-type NCTE, infects activated huPBMCs. Furthermore, in constructing the attenuated retrovirus of the invention, additional elements of the retrovirus which are essential for its replication and/or pathogenicity can also be disabled or eliminated, such as Nef, as explained below.

In normal mammalian cells, message RNA, present in the cell as ribonucleoprotein (RNP) complexes, is only exported from the nucleus to the cytoplasm after splicing is completed. To circumvent the requirement of splicing prior to export from the nucleus, all retroviruses have evolved a mechanism that allows the nuclear export of unspliced form of viral RNAs which are necessary for the production of structural proteins and essential for viral replication. This mechanism involves the highly structured NCTE cis-acting RNA element and its corresponding trans-acting RNA binding proteins, as discussed above. In simian type retroviruses, the NCTE is termed "CTE" (see Bray (1994) supra; Zolotukhin (1994) supra), and binds to endogenous cellular RNA binding proteins. In contrast, HIV-1's NCTE does not bind cellular NCTE-binding proteins. It encodes its own NCTE binding protein, called "Rev." Rev interacts with a specific HIV-1 NCTE sequence, designated the "Rev-responsive element," or "RRE," contained in its gag/pol and env encoding transcript. Rev interacts directly with RRE as part of the RNA export machinery which transports RRE-containing transcripts to the cytoplasm from the nucleus. As a result, HIV-1 needs both RRE and Rev to produce infectious virus. Disabling either produces a non-replicative, non-virulent virus. Replacing (i.e., reconstituting) HIV-1's RRE/Rev RNA transport mechanism with a less efficient NCTE, such as the PRE of the invention, produces an attenuated and avirulent hybrid virus.

To engineer a non-functional RRE and/or Rev, the skilled artisan can delete and or mutate any portion of the RRE or Rev coding sequence. Means to delete or mutate nucleic acid sequence are described herein, and are well known in the art. Construction of exemplary, attenuated retroviruses are also discussed in the Examples, below. RRE and Rev sequences are well known in the art, e.g., see databases, such as the NCBI database at http:/www.ncbi.nlm.nih.gov/Entrez/ nucleotide.html or http://www.ncbi.nlm.nih.gov/Entrez/ protein.html. Further description and sequence of HIV-1 Rev can be found in, e.g., Salminen (1997) *J. Virol.* 71:2647–2655, Accession U86770; Theodore (1996) *AIDS Res. Hunt. Retroviruses* 12:191–194, Accession AF004394; Fang, et al., Accession AF003887; Howard (1996) *AIDS Res. Hum. Retroviruses* 12:1413–1425, Accession L39106; to name only a few. Further description and sequence of HIV-1 RRE can be found in, e.g., Salminen (1996) *JOURNAL AIDS Res. Hum. Retroviruses* 12:1329–1339, Accession U46016, WO 9202228-A5 20-FEB-1992, Accession A20711; Battiste (1994) *Biochemistry* 33:2741–2747; Battiste (1995) *J. Biomol. NMR* 6:375–389; Battiste (1996) *Science* 273:1547–1551; to name just a few.

The PRE of the invention can be inserted at any position in the disabled (lacking an endogenous NCTE) retroviral genome as long as the insertion does not inactivate the virus. The point of insertion can be designed or altered to modify the level of attenuation for a given PRE. In one embodiment of the invention, the PRE is inserted in the 3' untranslated region of a disabled retrovirus. In alternative embodiments, the PRE is inserted in the region of the disabled NCTE sequence (e.g., RRE in HIV-1) or the Nef region. Each potential point of insertion must be investigated individually for efficacy and level of attenuation. For example, as described in Example 1, the PRE of SEQ ID NO:1 has been inserted in the Nef region of a disabled HIV-1 construct, at nucleotide (nt) 8887 of pNL4-3 (as described in Example 1) to successfully generate a PRE-attenuated virus. However, when the site of insertion was at nt 8786, located between the env and nefgenes, the hybrid failed to generate infectious virus. Thus, each insertion site must be individually tested for its ability to accept a PRE sequence to generate an infectious and non-pathogenic hybrid.

To further engineer and modify a desired levels of nucleo-cytoplasmic transport, message stability, rate of virion growth, levels of attenuation, and the like, more that one PRE, or different PREs, or both, can be inserted into a given retroviral construct.

In constructing the attenuated retroviruses and vaccines of the invention, in addition to endogenous NCTE, other elements essential for the virus' replication and/or pathogenicity can also be disabled or eliminated. For example, genetic engineering of a Nef-negative retrovirus may produce a recombinant hybrid with a greater degree of attenuation. In the case of HIV-1, a functional Nef gene is important for development of high viremia and AIDS. Animals infected with Nef-deleted attenuated viruses are resistant to subsequent challenge with pathogenic wild-type viruses. Some individuals with long-term nonprogressive HIV-1 infection (no clinical or immunological signs of immuno-deficiency despite being HIV seropositive for over a decade) are infected with viruses having naturally occurring Nef deletions. To engineer a non-functional Nef, the skilled artisan can delete and or mutate any portion of the Nef coding sequence. Nef sequences are well known in the art, e.g., see databases, such as the NCBI databases described above. For examples of HIV-1 Nef nucleic acid and polypeptide sequences, see, e.g., Accession Nos. Y15123, U88826, Y15121, Y15120, Y15116, to name only a few. For a further description of Nef, see, e.g., Saksela (1997) supra; Greenberg (1997) supra; Luo (1997) *J. Virol.* 71:9531–9537; Luo (1997) *J. Virol.* 71:9524–9530; Okada (1997) supra.

VII. Delivery of Nucleotides into Cells

The nucleic acids and oligonucleotides of the invention, including expression cassettes and vectors expressing PRE, can be delivered into cells in culture, tissues and organisms for synthesis, mutation, screening and the like. For example, the invention provides for a method for screening for a post-transcriptional RNA nucleo-cytoplasmic transport element (NCTE) binding protein. The method involves contacting a PRE of the invention with a test compound and measuring the ability of the test compound to bind the NCTE. This screening technique can be used in intact cells. Inhibitory oligonucleotides of the invention, and vectors capable of expressing these sequences, are also transferred into intact cells in cell culture, tissues or intact organisms.

The nucleic acids and oligonucleotides of the invention can be transferred into a cell using a variety of techniques well known in the art. For example, oligonucleotides can be delivered into the cytoplasm spontaneously, without specific modification. Alternatively, they can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. For example, a DNA binding protein, e.g., HBGF-1, is known to transport oligonucleotides into a cell. See, e.g., Tseng (1997) *J. Biol. Chem.* 272:25641–25647; Satoh (1997) *Biochem. Biophys. Res. Commun.* 238:795–799, describing efficient gene transduction by Epstein-Barr-virus-based vectors coupled with cationic liposome and HVJ-liposome. Displaying ligands specific for target cells on the surface of a liposome targets the construct to a specific cell or organ in vivo. See, e.g., Huwyler (1997) *J. Pharmacol. Exp. Ther.* 282:1541–1546, describing receptor mediated delivery using immunoliposomes.

Cells can also be permeabilized to enhance transport of oligonucleotides into the cell, without injuring the host cells. See, e.g., Verspohl (1997) *Cell. Biochem. Funct.* 15:127–134; Kang (1997) *Pharm. Res.* 14:706–712; Bashford (1994) *Methods Mol. Biol.* 27, 295–305, describing use of bacterial toxins for membrane permeabilization; and for general principles of membrane permeabilization, see, e.g., Hapala (1997) *Crit. Rev. Biotechnol.* 17:105–122.

VIII. Preparation, Formulation and Administration of Attenuated Viral Vaccines Live PRE-attenuated retrovirus, such as HIV-1, can be grown and harvested from activated human peripheral mononuclear cells or from a variety of tissue culture cells, such as human 293 cell line, as described herein; see also, e.g., Eberlein (1991) *Virus Res.* 19:153–161; Parente (1996) *Gene Ther.* 3:756–760; Margolis (1997) *AIDS Res. Hum. Retroviruses* 13:1411–1420. Virion-containing supernatants are collected, and, typically, filtered. PRE sequences in the harvested, attenuated virus for use in vaccine formulations can be confirmed by conventional sequencing. The attenuated virus can be further purified, e.g., by ultrafiltration or ultra-centrifugation. The live, attenuated virus can be stored, e.g., by refrigeration, or on a long-term basis, by freezing in liquid nitrogen.

A formulation for administering the virus as a vaccine is prepared using, e.g., any physiologically acceptable buffer, such as saline or phosphate buffered saline (PBS). This can be stored in a frozen state. The formulation can also be freeze-dried, stored at room temperature, and reconstituted by adding appropriate volume of buffer. The vaccine pharmaceutical formulation can be in the form of a sterile injectable preparation, such as a sterile injectable aqueous or oleaginous suspension. This suspension can be formulated according to the known art using those suitable dispersing or wetting agents and suspending agents which have been mentioned above. The sterile injectable preparation can also be a solution or suspension in a nontoxic parenterally-acceptable diluent or solvent, such as a solution of 1,3-butanediol. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

The PRE-containing attenuated virus and vaccine formulations can also be co-administered with other reagents to boost or otherwise augment the anti-viral immune response. For example, they can be administered with an adjuvant, e.g., oil-in-water microemulsions or polymeric microparticles. Oil-in-water microemulsions are potent and safe adjuvants in humans and have been used with HSV-2, HIV-1 and influenza virus vaccines. Microparticles can be prepared from the biodegradable polymers, e.g., poly(lactide-co-glycolides). See, e.g., O'Hagan (1998) *J. Pharm Pharmacol.* 50:1–10.

The live attenuated viral vaccine of the invention can be administered using any acceptable route, as, e.g., by application to a mucosal surface, by injection, by inhalation (such as by aerosol) or other intranasal route, or by ingestion. For examples of inhalants, see Rohatagi (1995) *J. Clin. Pharmacol.* 35:1187–1193; Tjwa (1995) *Ann. Allergy Asthma Immunol.* 75:107–111; Fernandez-de Castro (1997) *Salud Publica Mex* 39:53–60. Injection of vaccine can be intravenous or intramuscular; see, e.g., Groswasser (1997) *Pediatrics* 100:400–403, as example of injection techniques for efficient intramuscular vaccine delivery. Administration by application to any mucosal surface, including, e.g., intraoral (sublingual, buccal, and the like), intranasal, intrarectal, intravaginal, or ocular. For examples of mucosal administration methods, see, e.g., Staats (1997) *AIDS Res Hum Retroviruses* 13:945–952; Okada (1997) *J. Immunol.* 159:3638–3647; Wu (1997) *AIDS Res Hum Retroviruses* 13:1187–1194.

The amount of virus (number of virions) per dose will vary depending on results of different titrations used in clinical trials. The range can range, e.g., from only a few infectious units, to about $10^4$ to $10^{10}$ infectious units (i.e., virions) per dose. Protocols and means to determine safety and efficacy used for other attenuated vaccines can be adapted and used with the novel reagents provided by the invention; see, e.g., Beishe (1998) *N. Engl. J. Med.* 338:1405–1412; Gruber (1997) *Vaccine* 15:1379–1384; Tingle (1997) *Lancet* 349:1277–1281; Varis (1996) *J. Infect. Dis.* 174:S330–S334; Gruber (1996) *J. Infect. Dis.* 173:1313–1319.

After the vaccine has formulated in an acceptable carrier, it can be placed in an appropriate container and labeled. For administration of the vaccine, such labeling would include, e.g., instructions concerning the amount frequency and method of administration. In one embodiment, the invention provides for a kit and instructional material teaching the indications, dosage and schedule of administration of the vaccine.

Selection of individuals who would benefit from receiving the live, attenuated vaccine of the invention include, but are not limited to, individuals who have a high risk of being exposed to HIV, such as intravenous drug users, individuals who may been exposed, as through a needle stick or transfusion, and individuals whose exposure to the virus has been confirmed, e.g., by a positive blood test.

The vaccine can be administered in conjunction with other treatment regimens, e.g., it can be coadministered or administered before or after any anti-viral pharmaceutical (see, e.g., Moyle (1998) *Drugs* 55:383–404) or a killed (completely inactivated) anti-HIV vaccine. The vaccine can be administered in any form of schedule regimen, e.g., in a single dose, or, using several doses (e.g., boosters) at dosages and time intervals to be determined by clinical trials.

The attenuated vaccine of the invention is considered efficacious, i.e., immunoprotective, if it elicits any protective or ameliorative humoral or cell-mediated anti-HIV response. Preferably, the vaccine of the invention will cause no side effects, clinically significant pathology, acceleration of onset of symptoms, further dissemination of virus in the body, and the like. The anti-HIV response can be assessed by any parameter, e.g., by measuring the levels of anti-viral antibodies or HIV-specific T cells, the amount of HIV virion or nucleic acid in the blood or lymph nodes (see, e.g., Brown (1997) *Transfusion* 37:926–929), the levels of circulating helper (CD4$^+$) T cells, and the like. See also, O'Brien (1997) "Changes in plasma HIV RNA levels and CD4$^+$ lymphocyte counts predict both response to antiretroviral therapy and therapeutic failure," *Ann. Intern. Med.* 126:939–945; Hughes (1997) "Monitoring plasma HIV-1 RNA levels in addition to CD4$^+$ lymphocyte count improves assessment of antiretroviral therapeutic response," *Ann. Intern. Med.* 126:929–938; Burgisser (1997) "Monitoring responses to antiretroviral treatment in human immunodeficiency virus type 1 (HIV-1)-infected patients by serial lymph node aspiration," *J. Infect. Dis.* 175:1202–1205.

IX. Screening for NCTE Binding Proteins Using PRE

The invention provides for cell-based and in vitro assay systems to screen for novel NCTE-binding proteins using the PRE of the invention. The full-length PRE can be utilized, or, alternatively, a portion of a PRE can be used to assay for NCTE binding proteins. One embodiment of the invention provides for a method of screening for an NCTE binding protein by contacting a PRE of the invention with a test compound and measuring the ability of the test compound to bind the NCTE. Many assays are available that screen for nucleic acid binding proteins and all can be adapted and used with the novel reagents provided for by the invention. A few illustrative example are set forth below.

A variety of well-known techniques can be used to identify polypeptides which specifically bind to nucleic acids, such as PRE. For example, mobility shift DNA-binding assays, methylation and uracil interference assays, DNase and hydroxy radical footprinting analysis, fluorescence polarization, and UV crosslinking or chemical cross-linkers, can be used. For a general overview of protein-nucleic acid binding assays, see, e.g., Ausubel (chapter 12, DNA-Protein Interactions).

One technique for isolating co-associating proteins, including nucleic acid and DNA/RNA binding proteins, includes use of UV crosslinking or chemical cross-linkers, including, e.g., cleavable cross-linkers dithiobis (succinimidylpropionate) and 3,3'-dithiobis (sulfosuccinimidyl-propionate); see, e.g., McLaughlin (1996) *Ann. J. Hum. Genet.* 59:561–569, Tang (1996) *Biochemistry* 35:8216–8225; Lingner (1996) *Proc. Natl. Aca. Sci. U.S.A.* 93:10712; Chodosh (1986) *Mol. Cell. Biol* 6:4723–4733. If a specific protein is believed to bind to PRE, and an antibody is available or can be generated for that protein, co-immunoprecipitation analysis can be used. Alternatively, PRE-affinity columns can be generated to screen for potential PRE-binding proteins. In a variation of this assay, PRE-containing nucleic acid is biotinylated, reacted with a solution suspected of containing a PRE-binding protein, and then reacted with a strepavidin affinity column to isolate the PRE-containing nucleic acid/binding protein complex (see, e.g., Grabowski (1986) *Science* 233:1294–1299; Chodosh (1986) supra). The protein can then be conventionally eluted and isolated.

Mobility shift DNA-protein binding assay using nondenaturing polyacrylarnide gel electrophoresis is an extremely rapid and sensitive method for detecting polypeptides binding to DNA (see, e.g., Chodosh (1986) supra, Carthew (1985) *Cell* 43:439–448; Trejo (1997) *J. Biol. Chem.* 272:27411–27421; Bayliss (1997) *Nucleic Acids Res.* 25:3984–3990). Interference assays and DNase and hydroxy radical footprinting can be used to identify specific residues in the nucleic acid protein-binding site, see, e.g., Bi (1997) *J. Biol. Chem.* 272:26562–26572; Karaoglu (1991) *Nucleic Acids Res.* 19:5293–5300. Fluorescence polarization is a powerful technique for characterizing macromolecular associations and can provide equilibrium determinations of protein-DNA and protein-protein interactions. This technique is particularly useful to study low affinity protein-protein interactions, see, e.g., Lundblad (1996) *Mol. Endocrinol.* 10:607–612.

Proteins identified in by these techniques can be further separated on the basis of their size, net surface charge, hydrophobicity and affinity for ligands. In addition, antibodies raised against such proteins can be conjugated to column matrices and the proteins immunopurified. All of these general methods are well known in the art. See, e.g., Scopes, R. K., Protein Purification: Principles and Practice, 2nd ed., Springer Verlag, (1987). Chromatographic techniques can be performed at any scale and using equipment from many different manufacturers (e.g., Pharmacia Biotech).

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

The following examples are offered to illustrate, but not to limit the claimed invention.

Example 1

Identification, Isolation and Characterization of PRE of the Invention

The following example details the identification, isolation and characterization of PRE nucleic acids of the invention and their efficacy as attenuating agents in live HIV-1 vaccines.

Introduction

A Rev(−)/RRE(−) deficient HIV-1 hybrid was constructed and used to characterize a new cis-acting post-transcriptional regulatory element (PRE). This novel nucleic acid sequence functions as a nucleo-cytoplasmic transport element (NCTE), i.e., an RNA sequence participating in the cellular mechanism that transports transcripts from the nucleus to the cytoplasm. When PRE is used to replace the NCTE system of HIV-1 (Rev/RRE), the resultant hybrid virus is slower-growing and non-pathogenic. Most significantly, the PRE-attenuated construct is not cytopathic. The novel PRE sequence was initially isolated from a mouse genome. Computer analysis showed that the identified PRE has strong homology with some IAP sequences. Thus, the invention encompasses a novel family of PRE having different primary sequences and predicted RNA secondary structure from any previously identified NCTEs, including type D retrovirus CTEs, such as SRV-1. Thus, it is expected that the PRE of the invention specifically interact with novel PRE-specific binding proteins. The invention provides the novel reagents and methods for identifying such new RNA binding proteins. These results also demonstrate that defective HIV-1 hybrids are useful tools in identifying cellular genomic and RNA sequences that participate in post-transcriptional regulation.

Several viruses carry cis-acting sequences which regulate post-transcriptional steps of gene expression in a positive or negative fashion. HIV-1's NCTE, designated the "Rev responsive element," or "RRE," was identified within the env coding region of HIV-1 (Felber (1989) supra; Hadzopoulou-Cladaras (1989) supra; Malim (1989) supra). Additional NCTEs have been identified in type D retroviruses, in some type C retroviruses, in intracisternal A retroelements (IAPs), and in Hepatitis B virus. The type D retroviruses simian retrovirus-1 (SRV-1), SRV-2, and MPMV contain an NCTE located between the end of env and the 3' LTR. These NCTEs can replace HIV-1's NCTE (RRE), and produce an infectious, attenuated virus. Structure/function analysis of SRV-1, SRV-2, and MPMV NCTEs (termed "CTE" in type D retroviruses) revealed the importance of both primary and secondary structure for function. The predicted structures of type D CTEs show a strong conservation of secondary structure. Common features (i.e., loops, hairpins) are located in similar positions in different type D CTEs. In Tabemero (1997) *J. Virol.* 71:95–101, data-bank searching for NCTE-like elements sharing nucleotide sequences and secondary structure with the type-D CTEs found a similar NCTE in a type-A rctrovirus.

Rev/RRE-deficient hybrid HIV-1 viruses containing the type-D or type-A NCTEs have been propagated successfully after cell free infection in human PBMCs over long periods of time maintaining a stable Rev(−)/RRE(−) genotype (Zolotukhin (1994) supra). This demonstrated that NCTE-containing HIV-1 hybrids are relatively stable.

Identification of a Novel PRE

To identify new PREs in the mammalian genome, random fragments of heterologous genomic DNA were inserted in a Rev(−)RRE(−) hybrid HIV-1 virus (the defective virus constructed as described below, see Zolotukhin (1994) supra). These insert-containing hybrids were tested for the ability to replicate in human cell lines. Only nucleic acid segments that can functionally replace HIV-1's RRE and promote post-transcriptional activation result in virus propagation. Analysis of the functional genomic DNA, described below, identified a new family of PRE whose both primary sequence and computer predicted secondary structure is different from the previously identified NCTEs. "Core" PRE sequences are identified in SEQ ID NO:1 and SEQ ID NO:5. Data bank analysis revealed a very strong similarity of the PRE family of the invention with the genome of some defective endogenous retroviruses that belong to the murine intracistemal A particle (IAP) family.

As a first step, an NCTE (Rev/RRE)-deficient recombinant clone of HIV-1 was constructed. Briefly, an infectious HIV-1 (pNL4-3, Adachi (1986) *J. Virol.* 59:284–291) was disabled to lack functional Rev protein and RRE, as described in Nasioulas (1994) *J. Virol.* 68:2986–2993, and Zolotukhin (1994) supra, respectively. 37 point mutations were introduced into the RRE that did not affect the overlapping env reading frame (Nasioulas (1994) supra). Two mutations that eliminated Rev were constructed. The first mutation eliminated the Rev initiation codon. The second mutation introduced a stop codon in the 23rd amino acid of the Rev protein (Zolotukhin (1994) supra). This virus was designated NL43Rev(−)R(−). It is non-infectious. NL43Rev(−)R(−) does not produce detectable levels of viral structural proteins after transfection in HIV-susceptible cell lines. In addition, it cannot revert to wild type.

Using the same strategy as Zolotukhin (1994) supra, a unique Xho I site in the Nef region of NL43Rev(−)R(−) (at nucleotide 8887 of NL4-3) was exploited to insert putative PREs. Random genomic fragments were generated by partial restriction enzyme digestion of DNA extracted from mouse embryonic stem cells with Alu I and Rsa I (both blunt end cutters). Fragments of 1.5 to 0.4 kb in size were isolated by agarose gel electrophoresis and ligated into Xho I digested and filled-in (blunt-ended) NL43Rev(−)R(−) vector. The ligation mixtures were directly transfected into human 293 cells by standard calcium phosphate coprecipitation technique. Two additional hybrid HIV-1 clones were transfected in parallel; an NL43Rev(−)R(−) hybrid into which a SRV-1-derived CTE was inserted ("pR(−)Rev(−).S," described in Zolotukhin (1994) supra; and the starting disabled HIV-1 NL43Rev(−)R(−).

One day later, the 293 cells were co-cultivated with a CD4(+)-expressing, HIV-permissive Jurkat cell line to test for cell to cell virus transmission and propagation. At day 14 post-transfection, syncytia formation was detected and $p24^{gag}$ was expressed (detected by $p24^{gag}$ antigen assay) in some of the cells transfected with mouse genomic DNA. Virus from the positive clones was isolated for further analysis. Cells infected with R(−)Rev(−).S, containing the SRV-1 CTE, also formed syncytia and expressed $p24^{gag}$. Mock-transfected and starting vector NL43Rev(−)R(−)-transfected cells did not show any virus production.

Hybrid mouse DNA-containing HIV-1 from cell cultures positive for virus propagation were isolated and studied by PCR to identify the genomic inserts capable of "rescuing" the PRE-defective NL43Rev(−)R(−). PCR primers flanking the Xho I cloning site (Nef region sequences) were used to amplify and detect the presence of the genomic inserts. Agarose electrophoresis isolated different sized inserts in multiple bands of approximately 700 to 1100 base pair (bp) lengths.

natants were obtained from these co-cultivations, filtered and used to infect Jurkat cells. Successful infection of the Jurkat cells by virus-containing supernatant demonstrated that some of the PRE-rescued hybrids can infect Jurkat cells in a cell-free manner. Inserts from these infectious hybrids were isolated and sequenced. Analysis and comparison of these sequences revealed a novel nucleic acid sequence present in all of the "rescuing" inserts, designated "PRE7":

```
5'-CTTTCGCCATGGTAGCATAGGCTTTTGCTGCAGTGGAGGCGGACAATCTCC  (SEQ ID NO:4)
TCAGATTCGGTTTGCCGCTCTAAAAGAAATTATGCTGCGTTATGCCGTGGGGTG
CGAGGCTAAGCACTGCACAGAGGATAGCTTGCTGTTGGCATCCTGTGGAAGGC
ACGTCTGATTGCATGAAGGTTCAGTGTCCTAGTTCCCTTCCCCCAGGAAAAAC
GACACGGGAGCTGGCCAAGACCTCTCTGGGTGATGAGCCTAAGGGATGGTTTT
GTGTAGGGCCCCTATGCTTGCACACTGGGGATCAGACCTCTACCTTCACCCAT
GAGGCTTGCTTGCAGCAATTAAGATCTGGCCATAGGTTAATTAACATCCTGGC
CTTTTGATGCACCTGCCACAAG-3'
```

It was next demonstrated that the PRE-rescued HIV-1 hybrids were able to be transmitted by cell free infection. Virus stocks were produced by 0.45 um membrane filtration from the supernatants of the Jurkat cultures at 24 days after transfection. The filtered supematants were used to infect human peripheral blood mononuclear cells (PBMCs). PBMC cell cultures were obtained and activated as described in Zolotukhin (1994) supra. Briefly, PBMC cell cultures were obtained from healthy, HIV-seronegative blood donors, isolated by density centrifugation. They were stimulated for three days with phytohemagglutinin (PHA) at 5 to 10 micrograms (ug) per ml. Equal amounts of each of the viruses from the filtered 293 supernatants were used to infect $5\times10^5$ activated PBMCs. Virus propagation was monitored over time using a $p24^{gag}$ antigen capture ELISA assay. Both a commercial ELISA assay (Cellular Products, Buffalo, N.Y.) (used according to manufacturer's instructions) and an in-house $p24^{gag}$ antigen capture assay (using standard techniques) was used. Virus was detected (by $p24^{gag}$ antigen assay) in the PBMCs. Because some of the hybrid viruses were infectious via cell to cell contact (293 cell to Jurkat cell) and cell-free transmission (by filtered supematant infecting PBMCs), PRE-containing genomic sequences can act as PREs, insofar as infectivity is restored. However, as described below, although infectious, the PRE of the invention produces a slow-growing, non-pathogenic retroviral hybrid.

Characterization of the Mouse PRE-Containing Sequence

To characterize the nucleic acid sequences able to "rescue" the disabled HIV-1, DNA inserts ftom mouse DNA-containing infectious hybrid viruses were amplified, cloned, and sequenced (as described above). Fourteen clones were analyzed. Sequence analysis revealed that most of the genomic inserts were similar in nucleotide sequence. Several sequenced inserts were 1086 nucleotides (nt) in length, while some others varied between 690 and 807 nt.

To verify that these mouse genomic fragments were able to function as "rescuing" PREs, they were individually inserted into Xho I linearized NL43Rev(−)R(−) (as had been done with the initial fragmented mouse genomic DNA). Each viral construct was transfected into 293 cells and co-cultivated with Jurkat cells, as described above. Super- To verify that this "PRE7" sequence is a functional PRE, inserts from these infectious HIV-1 hybrid clones were amplified by PCR. Again, as described above, each fragment was ligated to the NL43Rev(−)R(−) HIV-1 clone linearized by Xho I. The ligation was transfected in 293 cells. Co-cultivations with Jurkat cells were started one day post-transfection. Two of the PRE7-containing hybrids were able to propagate in the co-cultivation assay. The infectivity of these clones was confirmed by subsequent cell free infections in Jurkat cells. Isolation, sequencing and analysis of their genomic inserts identified a core PRE region of 231 nucleotides (designated "fragment B"):

```
                                              (SEQ ID NO:1)
5'-GTGGGGTGCG AGGCTAAGCA CTGCACAGAG GATAGCTTGC
   TGTTGGCATC CTGTGGAAGG CACGTCTGAT TGCATGAAGG
   TTCAGTGTCC TAGTTCCCTT CCCCCAHHAA AAACGACACG
   GGAGCTGGCC AAGACCTCTC TGGGTGATGA GCCTAAGGGA
   TGGTTTTGTG TAGGGCCCCT ATGCTTGCAC ACTGGGGATC
   AGACCTCTAC CTTCACCCAT GAGGCTTGCT T-3'
```

SEQ ID NO:1 is located within the PRE7 (SEQ ID NO:4) fragment, as identified by the underlined nucleic acid residues in the above-described PRE7 sequence.

To demonstrate that the 231 bp fragment B is sufficient to rescue replication of the NL43Rev(−)R(−) hybrid, it was spliced into NL43Rev(−)R(−) and introduced into 293 and Jurkat cells by transfection/co-cultivation, as described above. Two independent fragment B-containing NL43Rev(−)R(−) hybrids produced infectious virus. Fragment B inserted in antisense orientation and the starting vector without any insert were uninfectious. Fragment 3-containing NL43Rev(−)R(−) was able to propagate in Jurkat cells after cell-free infection.

Further experimentation with the PRE7 (SEQ ID NO:4) sequence demonstrated another functional fragment (named "M4") 226 nt in length. It is very similar to the core fragment B (SEQ ID NO:1), having 7 additional nucleotides at the 3' end and and 2 fewer nucleotides at the 5' end:

(SEQ ID NO:5)
```
CCGTGGGGTGCGAGGCTAAGCACTGCACAGAGGATAGCTTGCTGTTGG
CATCCTGTGGAAGGCACGTCTGATTGCATGAAGGTTCAGTGTCCTAGT
TCCCTTCCCCCAGGAAAAACGACACGGGAGCTGGCCAAGACCTCTCTG
GGTGATGAGCCTAAGGGATGGTTTTGTGTAGGGCCCCTATGCTTGCAC
ACTGGGGATCAGACCTCTACCTTCACCCATGAGG.
```

PRE of the Invention Produce Attenuated Hybrid Retrovirus

The PRE of the invention, when inserted in RRE(−)Rev (−) HIV-1, are capable of functioning as NCTEs to "rescue" the disabled virus. When the PRE-containing hybrid HIV-1 virus infects activated human PBMCs, the level of expression of HIV-1 p24$^{gag}$ is between about 5 fold and about 200 fold less than levels of p24$^{gag}$ expression when HIV-1 wild type virus, utilizing wild-type NCTE, infects activated huPBMCs. The infectivity of PRE-containing RRE(−)Rev (−) hybrids were also compared to RRE(−)Rev(−) HIV-1 containing SRV-1 CTE (these clones are designated "R(−)Rev(−).S", as described in Zolotukhin (1994) supra). SEQ ID NO:1 (in the sense orientation)-containing hybrids; SEQ ID NO:1 (in the antisense orientation)-containing hybrids; SRV-1 CTE-containing hybrids, and starting vector RRE(−)Rev(−) were tested in parallel. Jurkat cells were infected by cell-free virus preparations. Virus production was monitored for the next ten days by measuring levels of p24$^{gag}$ expression in each cell culture. In one set of experiments, the level of attenuation of SEQ ID NO:1-containing hybrids was approximately equivalent to SRV-1 CTE-containing hybrids. p24$^{gag}$ expression peaked between five and seven days after cell-free infection. These results indicate a level of attenuation between about 10 fold and about 50 fold less (based on p24$^{gag}$ expression) as compared to comparable infection by HIV-1 wild type virus.

Sequence Analysis and Secondary Structure

Sequence identity comparisons of the PRE of the invention (SEQ ID NO:1), the "core" PRE identified within fragment 3B, was performed. Homologous sequences were identified by this computer search revealing a very strong similarity with the genome of some defective endogenous retroviruses belonging to the murine intracistemal A particle (IAP) family of retrotransposons. The homologous sequences were endogenous retroelements from mouse and hamster. In most cases, they contain a 3' LTR in a fixed position downstream of the region homologous to the PRE of SEQ ID NO:1. Secondary structure predictions were made using MFOLD (University of Wisconsin Genetics Computer Group package). MFold is an adaptation of the MFold package by Zuker and Jaeger, see Zuker (1989) *Science* 244:48–52; Jaeger (1989) *Proc. Natl. Acad. Sci. USA* 86:7706–7710. It showed that nucleotides within the 231 bp core element (SEQ ID NO:1) could be folded into a base-paired, double stranded region, a so-called "hairpin," forming a strong secondary structure. This secondary structure is conserved in all IAP elements identified in the database by sequence homology. The double stranded region is similar in all of the homologous sequences. However, the loop of the hairpin was not conserved. Significantly, the PRE of the invention have sufficiently different primary sequences from these IAP elements to predict a unique RNA secondary structure distinct from any previously identified NCTEs, including those from type D retrovirus CTEs, such as SRV-1. One or several of the functions of PRE of the invention may utilize this secondary structure. For example, the secondary structure may interact with trans-acting cellular factors, or be necessary for nucleo-cytoplasmic transport, transcript stability or expression, and the like. However, the ability of the PRE of the invention to act as an NCTE and an attenuating agent when inserted in disabled retroviruses is not limited by its ability to form any secondary structure or any form of secondary structure.

Sequence Identity Analysis to Identify PRE of the Invention

Sequence identity analysis is used to determine whether a nucleic acid is within scope of the invention. To identify a specie of the PRE family of the invention, a nucleic acid must have at least 80% nucleic acid sequence identity to a sequence set forth in SEQ ID NO:1. Publicly available nucleic acid databanks were searched for sequence identity (homology) to the exemplary SEQ ID NO:1 PRE of the invention. Specifically, the program PileUp was used, with the parameters: symbol comparison table: GenRunData:pileupdna.cmp, GapWeight:2, GapLength-Weight: 1. The following PRE sequence, having about 83% sequence identity to SEQ ID NO:1, was identified: AGGAGTTGCA AGGCTAAGC X ACTGCACAGG AGAGG X TCTG CGG XX TATAA CGACTTTCTC CTGGGAGATA AGTCATCTTG CATGAAGGTT CTATG X TCAT, where X is any nucleotide (SEQ ID NO:6).

SEQ ID NO:6 is a subsequence of a 7951 base pair long sequence submitted as Genbank Accession Nos. M10134, K02288, and K02289; described by Ono (1985) *J. Virol.* 55:387–394; Ono (1983) *Nucleic Acids Res.* 11:7169–7179. The sequence was isolated from a Syrian hamster and is homologous to intracistemal A-particle (IAP) genes.

Example 2

CTE-Containing HIV-1 are Attenuated In Vivo

The following example details use of post-transcriptional regulatory elements (PREs) as attenuating agents in HIV-1 infection and AIDS pathogenesis. To effect this attenuation, the exogenous PREs act in place of HIV-1's wild-type Rev/RRE post-transcriptional regulatory system. The efficacy the PRE of the invention as an HIV-1 attenuating agent in vivo can be demonstrated using functionally analogous NCTEs, such as the SRV-1 CTE. Hybrid HIV-1 clones were used in which the post-transcriptional regulatory element, or more specifically, the NCTE, from SRV-1 ("CTE") was inserted to replace the wild type HIV-1 NCTE (RRE). The "R(−)Rev(−).S" hybrid clones, described above (from Zolotukhin (1994) supra) were used. These hybrids were used in a SCID-hu mouse model to demonstrate the attenuating effect of the PRE of the invention ("PRE(+)") in RRE(−)Rev(−) HIV-1. Specifically, viral replication and cytopathic effects on lymphocytes were measured in vivo using art-recognized animal models.

R(−)Rev(−).S infect a Thy/Liv implant (Kollmann (1995) supra) in SCID-hu mice. Significantly, these PRE-attenuated viruses propagated slower than wild-type and Nef-negative (otherwise NCTE wild-type) HIV-1 clones. Levels of circulating CD4$^+$ lymphocytes were monitored for 6 weeks after initial infection. No depletion of CD4$^+$ cells was observed. This demonstrates an attenuated phenotype for cytotoxicity of the PRE-containing R(−)Rev(−).S HIV-1 clones. Direct comparison to a Nef-negative HIV-1 clone showed that the PRE attenuated viruses are less cytotoxic, independent of the absence or presence of Nef. Therefore, the replacement of HIV-1's wild-type NCTE (RRE) with SRV-1 NCTE is responsible for the distinct, non-cytotoxic (non-CD4$^+$ lymphocyte depleting) phenotype of the slowly replicating hybrid HIV-1.

The attenuation of the PRE-attenuated HIV-1, R(−)Rev(−).S, was further demonstrated by measuring its lower replicative capacity in vivo in an art-recognized animal model, the SCID-hu mouse (see Aldrovandi (1993) *Nature* 363:732–736; Bonyhaki (1993) *Nature* 363:728–732). The SCID-hu mice are produced by surgical implantation of human fetal liver and thymus under the kidney capsule of severe combined immunodeficient (SCID) mice. Normal T-cell differentiation has been shown to occur in the Thy/Liv implant. This is an art-recognized system for the study of HIV-1 infection and viral cytotoxicity in human lymphopoictic tissue. Normally, infection by wild type (wt) HIV-1 results in depletion of CD4+ T cells. Significantly, infection with HIV-1, resulting in low levels of viral replication, did not cause CD4+ cell depletion in vivo.

To further assess the attenuation of R(−)Rev(−).S, virus load and cytotoxicity after infection in SCID-hu mice was measured. Four different HIV-1 hybrids were tested: wt HIV-1 (NL4-3, described above); wt HIV-1 (NL4-3)/Nef negative; PRE(SRV-1 CTE)(+)/Nef(+), i.e., R(−)Rev(−).S; and PRE(SRV-1 CTE)(+)/Nef(−), i.e., R(−)Rev(−).S lacking Nef). 1000 infectious units per mouse are typically used to establish good SCID-hu infection (i.e., at least 50% to 90% infected) by attenuated strains of HIV-1, see Aldrovandi (1996) *J. Virol.* 70:1505–1511. Since the infectivity and replicative capacity of the PRE (SRV-1 CTE)-attenuated hybrids is reduced (as demonstrated by the experiments described above), the amount of input virus was increased. The SCID-hu mice were infected by injection of virus into the Thy/Liv implant at 500 to 850 TCID$_{50}$ in a final volume of 100 μl. Sequential biopsies of the implants were performed 3 and 6 weeks postinfection, and the samples were analyzed for virus replication by quantitative DNA-PCR and for the number of CD4+ thymocytes by flow cytometry (PCR and cytometry as described in Aldrovandi (1996) supra). All 7 mice infected by wt HIV-1 scored positive for HIV proviral sequences at 3 weeks postinfection. Depletion of CD4+ thymocytes (defined as measurement of less than 55% CD4+ cells in the thymocyte population) was detected in 2 of 7 mice at this time point, and in another 2 of 2 mice analyzed after 6 weeks. None of the mock-infected mice showed any sign of HIV infection or CD4+ thymocyte depletion. Replication of the NL4-3/Nef-negative hybrid was detectable in 2 of 10 mice after 3 weeks and in 8 of 9 mice at 6 weeks post-infection. Depletion of CD4+ thymocytes was found in 3 of 9 mice infected with NL-4-3/Nef-negative recombinants at 6 weeks postinfection (which is typical, as reported in Aldrovandi (1996) supra, and Jamieson (1994) *J. Virol.* 68:3478–3485).

In contrast, after infection with the PRE(SRV-1 CTE)(+) Nef(−) and PRE (SRV-1 CTE)(+) Nef(+) hybrids, provirus DNA was detectable only at the 6 week time point in 4 of 8 and 1 of 5 mice, respectively. The viral loads in the mice infected by the CTE(+) viruses were significantly lower than that of the RRE+/Nef-negative hybrids (i.e., wt except for lack of Nef). While implants infected by the RRE+/Nef-negative hybrids showed 3,000 to 28,000 provirus copies per $10^5$ cells, the PRE(+) Nef(−) virus contained about 500 to 2,400 copies per $10^5$ cells, resulting in about a 20-fold decrease in average provirus copies in the PRE(+)-attenuated virus-infected mice. In PRE(+) Nef(+) virus only 1 of 5 mice was provirus positive after 6 weeks. Analysis of the implants of all the mice infected by PRE(SRV-1 CTE)(+) viruses showed normal thymocyte profiles, i.e., no cytotoxicity. The virus' ability to produce Nef did not affect pathogenicity. These findings demonstrate that replacement of wt HIV-1 RRE with an exogenous PRE, in this case NCTE (CTE) from SRV-1, is primarily responsible for the slower growing, attenuated non-cytotoxic phenotype in the SCID-hu mouse model.

To address the question whether the lower virus load is responsible for the lower cytotoxicity of the PRE(SRV-1 CTE)-attenuated hybrids, the experiments were repeated using about 5-fold higher amounts of input viruses (approximately 2500 infectious units/mouse). Infection with these larger amounts of virus also does not lead to CD4+ thymocyte depletion. New stocks for PRE(SRV-1 CTE)(+)/Nef(−) and PRE(SRV-1 CTE)(+)/Nef(+) HIV clones with higher titers were generated yielding $5\times10^4$ and $4.7\times10^4$ TCID$_{50}$/ml, respectively. The Thy/Liv implants in SCID-hu mice were injected with 100 μl of these high titer stocks. Biopsies were analyzed at 3 and 6 weeks postinfection. At 3 weeks postinfection, no virus could be detected in the 6 mice infected with the either of the PRE(+)-attenuated HIV-1 hybrids. At 6 weeks postinfection, in all 4 mice infected by the PRE(SRV-1 CTE)(+)/Nef(−) hybrid and in all 7 mice infected by the PRE(SRV-1 CTE)(+)/Nef(+) hybrid, HIV-1 replication was detectable. Although the time necessary to detect the PRE(+) hybrid was still 6 weeks, the viral loads were clearly elevated, due to the higher amount of input viruses. The average proviral copies per $10^5$ cells was 15,000 in the case of CTE(+)/Nef(−) hybrid, which is similar to that obtained from mice infected with 5-fold lower amount of RRE+/Nef-negative clone. The virus load in the implants infected by the PRE(SRV-1 CTE)(+)/Nef(+) variant was at least ten-fold lower than that of the PRE(SRV-1 CTE)(+)/Nef(−) counterpart.

Interestingly, even with these differences in viral load, no significant changes were observed in the thymocyte profiles (within the time frame of the experiment, 6 weeks). Therefore, no depletion of CD4+ thymocytes by PRE(+) hybrids was observed. Parallel infections using wt HIV-1 resulted in high levels of virus load accompanied by loss of CD4+ cells. In conclusion, increasing the virus inocula did not increase the low cytotoxicity of the PRE(SRV-1 CTE)(+)-attenuated viruses in vivo, as observed in this SCID-hu mice model. Therefore, replacement of wt HIV-1 RRE with a PRE (SRV-1 CTE) produced HIV-1 hybrids that are less cytotoxic and more attenuated than Nef-negative (otherwise wt) HIV-1.

In conclusion, experiments using a PRE (SRV-1 CTE) functionally analogous to the PRE of the invention demonstrate the efficacy of PRE as attenuating agents in HIV-1 infection and AIDS pathogenesis in vivo. While PRE(SRV-1 CTE)(+) HIV-1 hybrids can infect a Thy/Liv implant in SCID-hu mice, they propagate slower than wt HIV-1 and NL4-3/Nef-negative hybrids. No depletion of CD4+ cells was observed in the PRE(+) hybrids, demonstrating an attenuated phenotype for cytotoxicity. Direct comparison to RRE+/Nef-negative HIV-1 showed that the exogenous PRE is responsible for attenuation independent of the absence or presence of Nef. Thus, these experiments demonstrate that PREs, such as the PRE of the invention exemplified by SEQ ID NO:1, can produce a slow-growing. attenuated HIV-1 hybrid in vivo.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. An isolated post-transcriptional regulatory element (PRE) nucleic acid comprising SEQ ID NO:1, the PRE nucleic acid defined as having the following property:

the PRE nucleic acid, when inserted in a recombinant, hybrid human immunodeficiency virus (HIV)-1 lacking or having a non-functional wild-type post-transcriptional RNA nucleo-cytoplasmic transport element (NCTE), functions as a NCTE in the hybrid HIV-1, and when the PRE-containing hybrid HIV-1 virus infects activated human peripheral blood mononuclear cells (huPBMCs), the level of expression of HIV-1 p24$^{gag}$ is between about 5 fold and about 200 fold less than levels of p24$^{gag}$ expression when HIV-1 wild type virus, utilizing wild-type NCTE, infects activated huPBMCs.

2. An isolated nucleic acid comprising a post-transcriptional regulatory element (PRE) nucleic acid inserted into a nucleo-cytoplasmic transport element (NCTE)-deficient hybrid virus clone, the PRE nucleic acid defined as having the following properties:

(i) when an encoded PRE-containing hybrid human immunodeficiency virus (HIV)-1 infects activated human peripheral blood mononuclear cells (huPBMCs), the level of expression of HIV-1 p24$^{gag}$ is between about 5 fold and about 200 fold less than levels of p24$^{gag}$ expression when HIV-1 wild type virus, utilizing wild-type NCTE, infects activated huPBMCs; and, (ii) the PRE nucleic acid has at least 80% nucleic acid sequence identity to the sequence set forth in SEQ ID NO:1.

3. The isolated nucleic acid of claim 2, wherein the PRE nucleic acid is inserted in place of a wild type nucleo-cytoplasmic transport element (NCTE).

4. The isolated nucleic acid of claim 2, wherein the virus is a retrovirus.

5. The isolated nucleic acid of claim 4, wherein the retrovirus clone is a HIV clone.

6. The isolated nucleic acid of claim 5, wherein the PRE nucleic acid comprises the sequence set forth in SEQ ID NO:1.

7. The isolated nucleic acid of claim 6, wherein when the PRE-containing hybrid HIV-1 virus infects activated huPBMCs, the level of expression of HIV-1 p24$^{gag}$ is between about 10 fold and about 50 fold less than levels of p24$^{gag}$ expression when HIV-1 wild type virus infects activated huPBMCs.

8. An expression cassette comprising a post-transcriptional regulatory element (PRE) nucleic acid operably linked to a promoter, wherein the PRE nucleic acid defined as having the following properties:

(i) the PRE nucleic acid, when inserted in a recombinant, hybrid human immunodeficiency virus (HIV)-1 lacking or having a non-functional wild-type post-transcriptional RNA nucleo-cytoplasmic transport element (NCTE), functions as a NCTE in the hybrid HIV-1, and when the PRE-containing hybrid HIV-1 virus infects activated human peripheral blood mononuclear cells (huPBMCs), the level of expression of HIV-1 p24$^{gag}$ is between about 5 fold and about 200 fold less than levels of p24$^{gag}$ expression when HIV-1 wild type virus, utilizing wild-type NCTE, infects activated huPBMCs.; and, (ii) the PRE has at least 80% nucleic acid sequence identity to the sequence as set forth in SEQ ID NO:1.

9. The expression cassette of claim 8, wherein the PRE nucleic acid is SEQ ID NO:1.

10. The expression cassette of claim 8, wherein the expression cassette is an expression vector.

11. A transfected cell comprising an expression cassette of claim 8.

12. A recombinant virus, wherein the virus either lacks or has non-functional endogenous post-transcriptional RNA nucleo-cytoplasmic transport elements (NCTEs), further comprising a post-transcriptional regulatory element (PRE) nucleic acid operatively inserted into the virus, wherein the PRE nucleic acid functions as an exogenous functional NCTE to reconstitute the lacking or non-functional endogenous NCTE and to reconstitute the infectivity of the virus in a mammalian cell, wherein the PRE nucleic acid has at least 80% nucleic acid sequence identity to the sequence as set forth in SEQ ID NO:1.

13. The recombinant virus of claim 12, wherein the virus is a retrovirus.

14. The recombinant virus of claim 12, wherein the PRE has at least 90% nucleic acid sequence identity to the sequence as set forth in SEQ ID NO:1.

15. The recombinant virus of claim 14, wherein the PRE comprises a sequence as set forth in SEQ ID NO:1.

16. The recombinant virus of claim 12, wherein when the PRE-containing hybrid HIV-1 virus infects activated huPBMCs, the level of expression of HIV-1 $p24^{gag}$ is between about 10 fold and about 50 fold less than levels of $p24^{gag}$ expression when HIV-1 wild type virus infects activated huPBMCs.

17. The recombinant virus of claim 12, wherein the virus is HIV-1.

18. The recombinant virus of claim 12, wherein the insertion of the PRE is in the 3' untranslated region of the virus.

19. The recombinant virus of claim 17, wherein the insertion of the PRE is in or flanking the Nef region of the HIV-1 virus.

20. The recombinant virus of claim 17, wherein the HIV-1 further lacks a functional Nef.

21. An immunogenic composition comprising an attenuated retrovirus, wherein the attenuated retrovirus, when administered in sufficient amounts is capable of eliciting an immune response to the retrovirus in a mammal with a functional immune system, wherein the attenuated retrovirus lacks an endogenous functional post-transcriptional RNA nucleo-cytoplasmic transport element (NCTE) and/or the ability to express an endogenous functional NCTE binding protein, and the attenuated retrovirus further comprises a post-transcriptional regulatory element (PRE) nucleic acid defined as having the following properties:

(i) the PRE nucleic acid, when inserted in a recombinant, hybrid human immunodeficiency virus (HIV)-1 lacking or having a non-functional wild-type post-transcriptional RNA nucleo-cytoplasmic transport element (NCTE), functions as a NCTE in the hybrid HIV-1, and when the PRE-containing hybrid HIV-1 virus infects activated human peripheral blood mononuclear cells (huPBMCs), the level of expression of HIV-1 $p24^{gag}$ is between about 5 fold and about 200 fold less than levels of $p24^{gag}$ expression when HIV-1 wild type virus, utilizing wild-type NCTE, infects activated huPBMCs.; and, (ii) the PRE has at least 80% nucleic acid sequence identity to the sequence as set forth in SEQ ID NO:1.

22. The immunogenic composition of claim 21, wherein the attenuated retrovirus is HIV-1.

23. The immunogenic composition of claim 21, wherein the insertion of the PRE is in the 3' untranslated region of the virus.

24. The immunogenic composition of claim 22, wherein the insertion of the PRE is in or flanking the Nef region of the HIV-1 virus.

25. The immunogenic composition of claim 22, wherein the attenuated HIV-1 further lacks a functional Nef.

26. A kit for eliciting an immune response to a virus in a mammal, the kit comprising an immunogenic composition and a pharmacologically acceptable carrier, wherein the immunogenic composition comprises an attenuated retrovirus, wherein the attenuated retrovirus, when administered in sufficient amounts is capable of eliciting an immune response to the retrovirus in a mammal with a functional immune system, wherein the attenuated retrovirus lacks an endogenous functional post-transcriptional RNA nucleo-cytoplasmic transport element (NCTE) and/or the ability to express an endogenous functional NCTE binding protein, and the attenuated retrovirus further comprises a post-transcriptional regulatory element (PRE) nucleic acid defined as having the following properties:

(i) the PRE nucleic acid, when inserted in a recombinant, hybrid human immunodeficiency virus (HIV)-1 lacking or having a non-functional wild-type post-transcriptional RNA nucleo-cytoplasmic transport element (NCTE), functions as a NCTE in the hybrid HIV-1, and when the PRE-containing hybrid HIV-1 virus infects activated human peripheral blood mononuclear cells (huPBMCs), the level of expression of HIV-1 $p24^{gag}$ is between about 5 fold and about 200 fold less than levels of $p24^{gag}$ expression when HIV-1 wild type virus, utilizing wild-type NCTE, infects activated huPBMCs.; and, (ii) the PRE has at least 80% nucleic acid sequence identity to the sequence as set forth in SEQ ID NO:1.

27. The kit of claim 26, further comprising an instructional material teaching the use of the immunogenic composition, wherein the instructional material indicates that the immunogenic composition is used for eliciting an immune response to HIV-1 in a mammal; that the immunogenic composition is to be administered to a mammal in a therapeutically effective amount sufficient to express a viral protein; wherein the immunogenic composition will not cause clinically significant CD4+ cell depletion; and, the expression of the viral protein elicits an immune response to the attenuated HIV-1 virus.

28. A method for eliciting an immune response to a virus in a mammal, comprising administering to a mammal a therapeutically effective amount of an attenuated recombinant virus, wherein the recombinant virus comprises a post-transcriptional regulatory element (PRE) defined as having the following properties:

(i) the PRE nucleic acid, when inserted in a recombinant, hybrid human immunodeficiency virus (HIV)-1 lacking or having a non-functional wild-type post-transcriptional RNA nucleo-cytoplasmic transport element (NCTE), functions as a NCTE in the hybrid HIV-1, and when the PRE-containing hybrid HIV-1 virus infects activated human peripheral blood mononuclear cells (huPBMCs), the level of expression of HIV-1 $p24^{gag}$ is between about 5 fold and about 200 fold less than levels of $p24^{gag}$ expression when HIV-1 wild type virus, utilizing wild-type NCTE, infects activated huPBMCs.; and, (ii) the PRE has at least 80% nucleic acid sequence identity to the sequence as set forth in SEQ ID NO:1.

29. The method of claim 28, wherein the virus is HIV-1.

30. An isolated post-transcriptional regulatory element (PRE) nucleic acid comprising SEQ ID NO:1, the PRE nucleic acid defined as having the following property:

(i) the PRE nucleic acid, when inserted in a recombinant, hybrid human immunodeficiency virus (HIV)-1 lacking or having a non-functional wild-type post-transcriptional RNA nucleo-cytoplasmic transport element (NCTE), functions as a NCTE in the hybrid HIV-1 to increase its protein expression and to produce functional virus; and (ii) the PRE nucleic acid, when inserted in a recombinant, hybrid human immunodeficiency virus (HIV)-1 lacking or having a non-functional wild-type post-transcriptional RNA nucleo-cytoplasmic transport element (NCTE), and when the PRE-containing hybrid HIV-1 virus infects activated human peripheral blood mononuclear cells (huPBMCs), the level of expression of HIV-1 p24$^{gag}$ is between about 5 fold and about 200 fold less than levels of p24$^{gag}$ expression when HIV-1 wild type virus, utilizing wild-type NCTE, infects activated huPBMCs.

* * * * *

SEQUENCE LISTING

<160> NUMBER OF SEQ ID NOS: 6

<210> SEQ ID NO 1
<211> LENGTH: 231
<212> TYPE: DNA
<213> ORGANISM: Artificial Sequence
<220> FEATURE:
<223> OTHER INFORMATION: Description of Artificial Sequence:core
      post-transcriptional regulatory element (PRE)
      designated "fragment B"

<400> SEQUENCE: 1
gtggggtgcg aggctaagca ctgcacagag gatagcttgc tgttggcatc ctgtggaagg      60
cacgtctgat tgcatgaagg ttcagtgtcc tagttccctt cccccaggaa aaacgacacg    120
ggagctggcc aagacctctc tgggtgatga gcctaaggga tggttttgtg tagggcccct    180
atgcttgcac actggggatc agacctctac cttcacccat gaggcttgct t             231

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence:illustrative
      primer oligonucleotide complementary to 3' thirty
      nucleic acids of SEQ ID NO:1

<400> SEQUENCE: 2
aagcaagcct catgggtgaa ggtagaggac                                      30

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence:illustrative
      primer oligonucleotide incorporating the 5' thirty
      nucleic acids of SEQ ID NO:1

<400> SEQUENCE: 3
gtggggtgcg aggctaagca ctgcacagag                                      30

<210> SEQ ID NO 4
<211> LENGTH: 391
<212> TYPE: DNA
<213> ORGANISM: Artificial Sequence
<220> FEATURE:
<223> OTHER INFORMATION: Description of Artificial Sequence:"rescuing"
      post-transcriptional regulatory element (PRE)
      insert designated "PRE7"

<400> SEQUENCE: 4
ctttcgccat ggtagcatag gcttttgctg cagtggaggc gggacaatct cctcagattc      60
ggtttgccgc tctaaaagaa attatgctgc gttatgccgt ggggtgcgag gctaagcact    120
gcacagagga tagcttgctg ttggcatcct gtggaaggca cgtctgattg catgaaggtt    180
cagtgtccta gttcccttcc cccaggaaaa acgacacggg agctggccaa gacctctctg    240
ggtgatgagc ctaagggatg gttttgtgta gggcccctat gcttgcacac tggggatcag    300
acctctacct tcacccatga ggcttgcttg cagcaattaa gatctggcca taggttaatt    360
aacatcctgg ccttttgatg cacctgccac a                                   391

-continued

```
<210> SEQ ID NO 5
<211> LENGTH: 226
<212> TYPE: DNA
<213> ORGANISM: Artificial Sequence
<220> FEATURE:
<223> OTHER INFORMATION: Description of Artificial Sequence:functional
      fragment named "M4"

<400> SEQUENCE: 5
ccgtggggtg cgaggctaag cactgcacag aggatagctt gctgttggca tcctgtggaa      60
ggcacgtctg attgcatgaa ggttcagtgt cctagttccc ttcccccagg aaaaacgaca    120
cgggagctgg ccaagacctc tctgggtgat gagcctaagg gatggttttg tgtagggccc    180
ctatgcttgc acactgggga tcagacctct accttcaccc atgagg                   226

<210> SEQ ID NO 6
<211> LENGTH: 100
<212> TYPE: DNA
<213> ORGANISM: Artificial Sequence
<220> FEATURE:
<223> OTHER INFORMATION: Description of Artificial Sequence:PRE sequence
      having about 83% sequence identity to SEQ ID NO:1
<220> FEATURE:
<221> NAME/KEY: modified_base
<222> LOCATION: (1)..(100)
<223> OTHER INFORMATION: n = any nucleotide

<400> SEQUENCE: 6
aggagttgca aggctaagcn actgcacagg agaggntctg cggnntataa cgactttctc      60
ctgggagata agtcatcttg catgaaggtt ctatgntcat                           100
```